(12) United States Patent
Ky et al.

(10) Patent No.: US 8,962,257 B2
(45) Date of Patent: Feb. 24, 2015

(54) METHODS FOR DIAGNOSING HEART FAILURE AND OTHER CARDIAC DISEASES

(75) Inventors: Bonnie Ky, Philadelphia, PA (US);
Thomas Cappola, Haverford, PA (US);
Douglas B. Sawyer, Nashville, TN (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 172 days.

(21) Appl. No.: 13/043,350

(22) Filed: Mar. 8, 2011

(65) Prior Publication Data
US 2011/0256562 A1 Oct. 20, 2011

Related U.S. Application Data

(60) Provisional application No. 61/311,658, filed on Mar. 8, 2010.

(51) Int. Cl.
 *G01N 33/53* (2006.01)
 *C07K 16/22* (2006.01)
 *G01N 33/68* (2006.01)

(52) U.S. Cl.
 CPC .... *G01N 33/6872* (2013.01); *G01N 2333/4756* (2013.01); *G01N 2333/58* (2013.01); *G01N 2800/32* (2013.01); *G01N 2800/50* (2013.01); *G01N 2800/52* (2013.01); *G01N 2800/56* (2013.01)

USPC ........... 435/7.1; 435/7.9; 435/7.94; 435/7.95; 530/387.1; 530/388.24

(58) Field of Classification Search
None
See application file for complete search history.

(56) References Cited

FOREIGN PATENT DOCUMENTS

WO   WO/03/057014   7/2003

OTHER PUBLICATIONS

Gilmour et al. (2002). Neuregulin expression, function, and signaling in human ovarian cancer cells. Clinical Care Research. 8:3933-3942.*

* cited by examiner

*Primary Examiner* — Joanne Hama
*Assistant Examiner* — Jon M Lockard
(74) *Attorney, Agent, or Firm* — Mark S. Cohen; Pearl Cohen Zedek Latzer Baratz LLP

(57) ABSTRACT

The invention relates to methods of diagnosing the severity of heart failure or a cardiac dysfunction in a subject. The invention further relates to monitoring the severity of heart failure in a subject and determining the prognosis of a subject that has suffered from heart failure. This invention also relates methods to identify patients at risk for cardiac dysfunction when exposed to cardiotoxic chemotherapy agents.

14 Claims, 14 Drawing Sheets

Figure 1: NRG-1 Signaling Pathway

Changes in NRG-1β with Doxorubicin and Herceptin

- With doxorubicin exposure, there is a significant decrease in NRG-1β over time

- Three months of herceptin exposure was not associated with a statistically significant change in NRG-1β

Visit:
1 PreAC
2 PreTH
3 PreH alone

Visit:
1 PreAC
2 PreTH
3 PreH alone

METHODS FOR DIAGNOSING HEART FAILURE AND OTHER CARDIAC DISEASES

CROSS-REFERENCE TO RELATED APPLICATIONS

This application claims priority to U.S. Provisional Patent Application 61/311,658, filed Mar. 8, 2010, which is incorporated by reference herein in its entirety.

GOVERNMENT INTEREST

The work described in this application was supported, in whole or in part, by grants from the National Institute of Health (Grant Numbers HL088577, HL068144, KL1RR024132, and HL095661). The United States government may have certain rights in the invention.

FIELD OF INVENTION

The invention relates to methods of diagnosing the severity of heart failure or cardiac dysfunction in a subject. The invention further relates to monitoring the severity of heart failure in a subject and determining the prognosis of a subject that has suffered from heart failure. This invention also relates to methods of predicting who is at risk for heart failure and cardiac dysfunction when exposed to cardiotoxic chemotherapeutic agents.

BACKGROUND OF THE INVENTION

Virtually all forms of heart failure are characterized at the cellular level by abnormalities in growth and survival of cardiac myocytes. Animal studies have shown that the epidermal growth factor Neuregulin-1 (NRG-1) is a critical regulator of these processes. NRG-1 is released from microvascular endothelial cells and acts as a paracrine growth factor via the ErbB family of tyrbsine kinase receptors expressed in cardiac myocytes to regulate myocyte growth, differentiation, and the stress response.

Important insights come from the cardiotoxic side effects of the chemotherapeutic agent trastuzumab (Herceptin®), a monoclonal antibody directed against ErbB2 (Her2) that blocks NRG-1/ErbB signaling and is used to treat receptor-positive breast carcinoma. Exposure to trastuzumab can induce a clinically significant cardiomyopathy that often reverses after discontinuation of therapy.

From a public health standpoint, cardiac remodeling is the central feature of congestive heart failure, which accounts for 6.5 million hospital days each year. Heart failure has now become the fourth leading cause of adult hospitalizations in the US, and in adults greater than 65 years of age, it is the leading cause of hospitalizations. Five million Americans suffer from chronic heart failure, and the prevalence of this condition is rising. Overall, the prognosis for heart failure patients is poor. In 2001, nearly 53,000 patients died of heart failure as the primary cause, and the number of heart failure deaths has increased over time.

Currently, novel mechanistic biomarkers can improve our understanding of the complex syndrome of heart failure and might be more useful as a multimarker strategy for establishing diagnosis, prognosis, and monitoring response to therapy.

Chemotherapy utilized in the treatment of breast cancer has potential negative effects on specific organs, with cardiac toxicity being a devastating complication associated with a poor prognosis. As both the incidence of breast cancer rises and the survival rates of patients improve, the magnitude of the problem has become increasingly significant. More than 2 million breast cancer survivors in the US alone are at risk for cardiotoxicity with the cardiovascular disease risk potentially exceeding that of recurrent cancer. Monoclonal antibodies such as trastuzumab, used to treat ErbB2 (Her-2) positive breast cancers, are associated with a 4-27% rate of heart failure and cardiac dysfunction worsened by anthracyclines.

Currently there is a lack of an established marker that is able to identify individuals at high risk of adverse cardiac events with exposure to chemotherapy. Accordingly, there exists a need to identify specific mechanistic biomarkers that are able to discriminate patients at risk for heart-failure and cardiac dysfunction when exposed to chemotherapy.

SUMMARY OF THE INVENTION

In one embodiment, the invention relates to a method for diagnosing heart failure severity in a subject at risk for heart failure, said method comprising: obtaining a biological sample from said subject; and analyzing said sample to determine the level of over-expression or under-expression of a biomarker associated with heart failure severity, and comparing said level of over-expression or under-expression to that of a pre-determined standard; wherein, and in another embodiment, said biomarker is NRG-1β.

In one embodiment, the invention relates to a method of monitoring response to therapy in a subject having suffered from heart failure said method comprising: obtaining a biological sample from said subject; and analyzing said sample to determine the level of over-expression or under-expression of a biomarker associated with heart failure severity, and comparing said level of over-expression or under-expression to that of a pre-determined standard; wherein, and in another embodiment, said biomarker is NRG-1β.

In another embodiment, the invention relates to a method of providing a prognosis for a subject having suffered from heart failure, said method comprising: obtaining a biological sample from said subject; and analyzing said sample to determine the level of over-expression or under-expression of a biomarker associated with heart failure severity, and comparing said level of over-expression or under-expression to that of a pre-determined standard; wherein, and in another embodiment, said biomarker is NRG-1β.

In one embodiment, the invention relates to a method for identifying a subject at risk of a chemotherapy-induced disease, said method comprising: obtaining a biological sample from said subject; and analyzing said sample to determine the level of over-expression or under-expression of a biomarker associated with heart failure severity, and comparing said level of over-expression or under-expression to that of a pre-determined standard; wherein, and in another embodiment, said biomarker is NRG-1β.

In another embodiment, the invention relates to a method for detecting a biomarker associated with heart failure severity in a subject, said method comprising: obtaining a biological sample from said subject; and analyzing said sample to determine the level of over-expression or under-expression of a biomarker associated with heart failure severity, and comparing said level of over-expression or under-expression to that of a pre-determined standard; wherein, and in another embodiment, said biomarker is NRG-1β.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings.

DETAILED DESCRIPTION OF THE INVENTION

Figure 1:
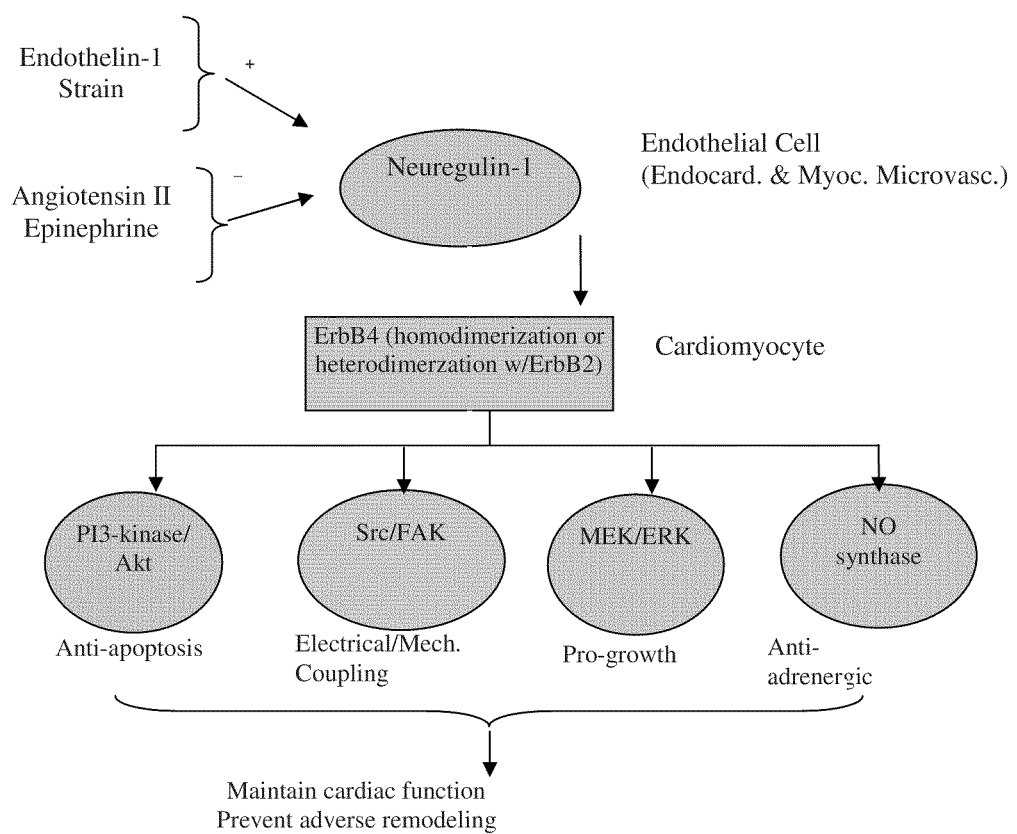
FIG. 1. Shows that NRG-1 is expressed in endocardial and myocardial microvascular endothelial cells, and ErbB2 and ErbB4 in cardiomyocytes where it binds to ErbB4, which then homodimerizes with itself or heterodimerizes with ErbB2. NRG-1, stimulated by factors such as endothelin-1, strain, injury, and ischemia, provokes a pro-survival and pro-growth response by activating a variety of downstream signaling pathways, including: Akt/PI3-kinase, MEK/ERK, Src/FAK, and NO synthase.

The invention provided herein relates in one embodiment to a method for diagnosing heart failure severity in a subject at risk for heart failure, the method comprising: obtaining a biological sample from the subject; analyzing said sample to determine the level of over-expression or under-expression of a biomarker associated with heart failure severity, and comparing said level of over-expression or under-expression to that of a pre-determined standard; wherein, and in another embodiment, said biomarker is NRG-1β.

In another embodiment, the term "nucleic acid" refers, in one embodiment, to the phosphate ester polymeric form of ribonucleosides (adenosine, guanosine, uridine or cytidine; "RNA molecules") or in another embodiment, to deoxyribonucleosides (deoxyadenosine, deoxyguanosine, deoxythymidine, or deoxycytidine; "DNA molecules").

In another embodiment, the invention relates to a method of monitoring response to therapy in a subject having suffered from heart failure said method comprising: obtaining a biological sample from said subject; analyzing said sample to determine the level of over-expression or under-expression of a biomarker associated with heart failure severity, and comparing said level of over-expression or under-expression to that of a pre-determined standard; wherein, and in another embodiment, said biomarker is NRG-1β.

In one embodiment, the invention relates to a method for providing a prognosis for a subject having suffered from heart failure, the method comprising: obtaining a biological sample from the subject; analyzing said sample to determine the level of over-expression or under-expression of a biomarker associated with heart failure severity, and comparing said level of over-expression or under-expression to that of a pre-determined standard; wherein, and in another embodiment, said biomarker is NRG-1β.

In another embodiment, the invention relates to a method for identifying a subject at risk of cardiotoxicity from cancer therapy, the method comprising: obtaining a biological sample from the subject; analyzing said sample to determine the level of over-expression or under-expression of a biomarker associated with heart failure severity, and comparing said level of over-expression or under-expression to that of a pre-determined standard; wherein and in another embodiment, said biomarker is NRG-1β. In another embodiment, cardiotoxicity from cancer therapy is cardiac dysfunction or heart failure. In another embodiment, the method enables monitoring said subject for cardiac dysfunction.

In another embodiment, alterations in circulating NRG-1β levels over time in breast cancer patients exposed to cardiotoxic cancer therapy are associated with incident cardiac dysfunction.

In another embodiment, the invention relates to a method for detecting a biomarker associated with heart failure severity in a subject, the method comprising: obtaining a biological sample from the subject; analyzing said sample to determine the level of over-expression or under-expression of a biomarker associated with heart failure severity, and comparing said level of over-expression or under-expression to that of a pre-determined standard; wherein and in another embodiment, said biomarker is NRG-1β. In another embodiment, the method further comprises the step of quantifying circulating NRG-1β levels, wherein said quantification is enabled by using a novel indirect sandwich enzyme-linked immunosorbant assay.

In one embodiment the invention further encompasses functional variants of the NRG-1β. In another embodiment, the NRG-1β is any such NRG-1β known in the art including, but not limited to, the following: NP_001153473, NP_001153471, NP_001153467, NP_039251, NP_039250.

In one embodiment, the NRG-1 system is critical in mediating the cardiac stress response. In another embodiment, in response to oxidative stress, NRG-1β expression increases in endothelial cell culture, and whole mouse hearts subjected to ischemia-reperfusion injury, NRG-1β is detected in the perfusate.

In another embodiment, the NRG-1/ErbB pathway, by promoting cell growth and survival and exerting beneficial neurohormonal effects, is a key modifier of adaptive remodeling and the cardiac stress response. In the adult animal, NRG-1 is expressed in endocardial and myocardial microvascular endothelial cells, and ErbB2 and ErbB4 in cardiomyocytes (FIG. 1). NRG-1 binds to ErbB4, which then homodimerizes or heterodimerizes with ErbB2, a major mediator of NRG-1's actions. NRG-1, stimulated by factors such as endothelin-1 and strain, ischemia and injury, provokes a pro-survival and pro-growth response by activating a variety of downstream signaling pathways, including: Akt/PI3-kinase, MEK/ERK, Src/FAK, and NO synthase (FIG. 1). These signals oppose apoptosis, stimulate myocyte growth, and enhance cell-to-cell coupling. In one embodiment, NRG-1β is involved in cardiomyocyte regeneration.

In one embodiment, an increase in circulating NRG-1β reflects an impaired compensatory response, and in another embodiment, said increase in circulation is secondary to either an augmentation in NRG-1β production or as a result of a reduction in receptor binding or activity. In another embodiment, the cardiac stress associated with heart failure leads to an increase in NRG-1β, and similar to natriuretic peptides like BNP, NRG-1β levels are a marker of the underlying severity of disease.

In another embodiment, the invention encompasses use of NRG-1β as a single or panel of biomarkers for potential clinical risk assessment. In another embodiment, this would lead to improved risk stratification and the use of directed therapy to modify known factors that are associated with worse outcomes.

In another embodiment, the methods provided herein further comprise jointly using first a NRG-1β biomarker and an additional biomarker. In another embodiment, the association of NRG-β with adverse outcomes is independent of the additional biomarker. In another embodiment the additional marker is BNP. In another embodiment, the assessment of the biomarkers jointly improves risk assessment over either marker alone in subjects with heart failure.

In another embodiment, the heart failure is ischemic heart failure, nonischemic heart failure, hypertensive heart disease, inflammatory heart disease, valvular heart disease, coronary heart disease, cardiomyopathy, cardiovascular disease, or cancer therapy-related disease.

In one embodiment, the subject is a human subject. In another embodiment, the subject is classified as having heart failure class I-IV according to the New York Heart Association (NYHA). In another embodiment, heart failure includes from class I-IV and both nonischemic and ischemic heart failure. In another embodiment, the relevance of circulating NRG-1β is more prominent in the class III/IV and ischemic groups. NYHA classes and associated symptoms include class I: No symptoms and no limitation in ordinary physical activity, e.g. shortness of breath when walking, climbing stairs etc. Class II: Mild symptoms (mild shortness of breath and/or angina) and slight limitation during ordinary activity. Class III: Marked limitation in activity due to symptoms, even during less-than-ordinary activity, e.g. walking short distances (20-100 m). Comfortable only at rest. Class IV: Severe limitations. Experiences symptoms even while at rest. Mostly bedbound patients. In another embodiment, the subject is being monitored for the heart severity. In another embodiment, the subject is undergoing chemotherapeutic therapy.

In one embodiment, subjects are stratified by cardiomyopathy etiology (ischemic versus nonischemic) and heart failure severity (NYHA Class I/II versus III/IV).

In one embodiment, the Penn Heart Failure Study (PHFS), is a cohort of subjects with predominantly systolic dysfunction and eccentric hypertrophy, In another embodiment, the Chronic Renal Insufficiency Cohort (CRIC) Study, is a cohort of subjects with renal dysfunction. In another embodiment, PHFS and CRIC represent the full spectrum of cardiac remodeling encountered in clinical practice and a detailed, analytic study of these patients enable which subjects are the most appropriate targets for such an intervention. The PHFS cohort represents a rich population of heart failure subjects with a predominance of eccentric hypertrophy and systolic dysfunction. CRIC includes all remodeling phenotypes in patients with an accelerated course of cardiac remodeling secondary to stimuli associated with renal dysfunction. In another embodiment, the use of these two diverse cohorts enable a comprehensive and systematic depiction of the biologic and clinical significance of circulating NRG-1β.

In another embodiment, NRG-1β is independently associated with heart failure characteristics. In another embodiment, NRG-1β is independently associated with transplant-free survival in a chronic heart failure cohort.

In one embodiment, provided herein is a method of determining the longitudinal relationship between circulating NRG-1β levels and left ventricular remodeling across the full spectrum of cardiac remodeling in a subject. In another embodiment, the subject has normal, concentric, or eccentric remodeling geometries. In another embodiment, longitudinal studies enable defining the patterns of circulating NRG-1β over time, and the effects of changes in NRG-1β level on changes in echocardiographic parameters of remodeling and survival. In another embodiment, defining a chronological sequence enables delineating a temporal relationship between exposure (NRG-1β level) and outcome (adverse cardiac event or remodeling parameter).

In another embodiment, sustained elevations in circulating NRG-1β levels are independently associated with a subsequent increased risk of hospitalization for heart failure and cardiovascular death. In yet another embodiment, circulating NRG-1β levels are associated with progressive concentric cardiac remodeling and hypertrophy in a linear fashion in a said subject.

Cardiac remodeling is the broad term used to describe changes in size, geometry, and function of the left ventricle that occur in response to physiologic and pathologic stress. Echocardiographically, this is defined by ventricular geometry and classified as normal, concentric remodeling, concentric hypertrophy, and eccentric hypertrophy. This classification system is based upon measures of relative wall thickness (RWT) and left ventricular mass. RWT is defined by 2× posterior wall thickness (PWT) divided by the left ventricular internal diameter at end-diastole (LVIDd), and ventricular mass is defined according to the Penn formula using the measures PWT, LVIDd, and septal wall thickness $(0.8 \times \{1.04 [(LVIDd+PWT+SWT)^3-(LVIDd)^3]\}+0.6 \text{ g})$.

In another embodiment, "concentric remodeling" refers to an increase in relative wall thickness and lack of cavity dilation with normal cardiac mass. In another embodiment, "hypertrophy" refers to the increase in the volume of an organ or tissue due to the enlargement of its component cells. In another embodiment, "eccentric hypertrophy" refers to the development of cavity dilation and lack of increase in wall thickness.

Concentric remodeling reflects an increase in relative wall thickness and normal mass; concentric hypertrophy is marked by both an increase in RWT and mass; and eccentric hypertrophy by an increase in cardiac mass but with a normal RWT. This latter phenotype is often associated with an increase in cardiac volume and decrease in function (i.e. dilated cardiomyopathy). Over time, in response to exogenous stimuli, the ventricle can transition from one geometric phenotype to another. In one embodiment, the pathophysiologic and molecular signals vary according to remodeling geometry, e.g. dilated or thickened.

In one embodiment, the level of expression of the biomarker is determined by comparing it to the level of expression of a standard. In another embodiment, the standard is taken from a subject or pool of subjects correctly diagnosed as being healthy. In another embodiment, the expression profile is a relative value as compared to a standard.

In one embodiment the term "standard" refers to pooled samples from healthy subjects. In another embodiment, it refers to pooled samples from subjects having heart failure, cardiac dysfunction, adverse conditions associated with heart failure, or adverse conditions as a result of having chemotherapeutic therapy. In another embodiment, it refers to pooled samples from subjects with known heart failure severity. In another embodiment, the standard may be ethnically- or gender- or age-matched recipients. It is to be understood that the standard may be derived from any subject, or pool of subjects, whose expression profile or profiles, once generated, is sufficient to detect even minute relative differences in expression, when compared to a test sample, or in another embodiment, to a subject that has heart failure, cardiac dysfunction, adverse conditions associated with heart failure, or adverse conditions as a result of having chemotherapeutic therapy. In another embodiment, a standard is determined as such by a skilled artisan.

In one embodiment, the standard is determined by the expression level profile in a healthy subject or pool of subjects. In another embodiment, the standard is the average expression level profile taken from a pool of subjects. In another embodiment, the standard is the average expression level of one biomarker of the invention taken from a pool of subjects. In another embodiment, the standard is the average expression level of at least one biomarker of the invention taken from a pool of subjects. In another embodiment, the standard is the mean expression level profile taken from a pool of subjects.

In another embodiment, the standard is the median expression profile level taken from a pool of subjects. In another embodiment, the standard is the median expression level of one biomarker of the invention taken from a pool of subjects. In another embodiment, the standard is the median expression level of at least one or more biomarkers of the invention taken from a pool of subjects.

In another embodiment, the method involves the detection of over-expression or under-expression of said biomarker. In another embodiment, the level of expression of the biomarker is indicative of the severity of the subject's condition. In yet another embodiment, the biomarker is over-expressed or under-expressed relative to the level of expression of a standard. In yet another embodiment, comparing the over-expression or under-expression of the biomarker to the level of expression of a standard enables measuring the severity of heart failure in the subject. In another embodiment, it enables diagnosing the severity of heart failure in the subject. In another embodiment, it enables monitoring the severity of heart failure in the subject. In another embodiment, it enables determining the prognosis of a heart failure in the subject. In another embodiment, it enables monitoring the therapeutic response of a subject having heart failure. In another embodiment, it enables monitoring said subject for cardiac dysfunction. In another embodiment, it enables measuring the incident cardiotoxicity in the subject.

In another embodiment the biomarker is over-expressed in blood, sera, plasma, saliva, sperm, urine, mucous, cerebral spinal fluid, or any combination thereof and such over expression is independently associated with heart failure or cardio-logical death. In another embodiment a biomarker is under-expressed in blood, sera, plasma, saliva, sperm, urine, mucous, cerebral spinal fluid, or any combination thereof.

In one embodiment, the level of expression of the biomarker is determined by methods known in the art and include, but are not limited to, PCR, Microarray assays, Immunoblots, notherns, ELISA, fluorescence-based methods (Immunofluorescence, FACS), mass spectrometry, and the like. In another embodiment, any other method known in the art is used for measuring/analyzing/quantifying the level of a biomarker provided herein.

In another embodiment, the term "expression" refers to the transcription and stable accumulation of sense (mRNA) or antisense RNA derived from the nucleic acid fragment or fragments of the invention. Expression also refers to, in one embodiment, the translation of mRNA into a polypeptide.

In one embodiment, the term "expression profile" refers to the results obtained upon differentially determining expression of the gene or genes encoding the biomarker provided herein, when compared to a standard. The profile is assigned to a given subject, which reflects comparative results between his or her expression encoding the biomarker as compared to a standard. In another, embodiment, the expression profile further comprises a determination of relative expression of nucleic acids, which do not code for a functional protein, as compared to the standard.

In another embodiment, the term "differentially expressed" refers to a relative abundance or absence of expression in a subject as compared to a standard. In yet another embodiment, the term "differential expression" refers to changed expression, either higher or lower, in the subject, as compared to the standard.

In one embodiment, differential gene expression includes, a comparison of expression between two or more genes, or in another embodiment, a comparison of the ratios of the expression between two or more genes, or in another embodiment, a comparison of two differently processed products of the same gene, which differ between control subjects and subjects that have or have had heart failure or a cardiac dysfunction, at any stage of the process. Differential expression refers in one embodiment to quantitative, as well as in another embodiment, qualitative, differences in the temporal or cellular expression pattern in a gene or its expression products as described herein.

In another embodiment the biomarker/biomarkers is/are expression is tissue-specific. In another embodiment, the biomarker/biomarkers is/are expression is global. In another embodiment, the biomarker/biomarkers is/are expression is systemic.

In one embodiment, the present invention encompasses several examples of a biological sample. In another embodiment, the biological sample is cells, or in another embodiment tissue or in another embodiment peripheral blood. In one embodiment, the biological sample is obtained from a normal subject. The biological sample may, in one embodiment, be a sample of body fluid. In another embodiment, biological samples refer to, blood, serum, plasma, sperm, urine, mucous, tissue biopsy, organ biopsy, synovial fluid, urine, bile fluid, cerebrospinal fluid, saliva, mucosal secretion, effusion, sweat or their combination. In another embodiment, the biomarker/biomarkers is/are expression is global. In another embodiment, the biomarker/biomarkers is/are expression is systemic. The proteins of the sample are in one embodiment distributed on various support matrices by methods specific to each matrix. Suitable matrices may, in one embodiment be paper, cellulose acetate, silica, glass, carbon, sugars, plastics and derivatives thereof, and a person skilled in the art will be familiar with the techniques of using such support matrices for the separation of proteins.

In one embodiment, a biological sample serves as the source for gene expression profile. In another embodiment, a gene expression profile is compiled using a sample of peripheral blood of a subject being evaluated.

In one embodiment, the gene expression profile compiled in the methods of this invention will comprise genes that are differentially expressed in subjects afflicted with heart failure or cardiac dysfunction. In another embodiment, the gene expression profile compiled in the methods of this invention will comprise genes that are differentially expressed in subjects predisposed to getting heart failure or cardiac dysfunction. In another embodiment, the pattern of the differentially expressed genes will comprise increased expression of biomarker genes in the afflicted subjects. In another embodiment, the biomarker gene encodes NRG-1β.

In another embodiment, the pattern of the differentially expressed genes result in differentially expressed biomarker(s) that enable monitoring the progression of or diagnosis of a subject that has or has had a heart failure or cardiac dysfunction. In another embodiment, the pattern of the differentially expressed genes result in differentially expressed biomarker(s) that enable determining the prognosis of a subject that has or has had heart failure or cardiac dysfunction. In yet another embodiment, the pattern of the differentially expressed genes result in differentially expressed biomarker(s) that enable determining a proper treatment method for a subject that has or has had heart failure or cardiac dysfunction.

"Marker" in the context of the present invention refers to a polypeptide which is differentially present in a sample taken from subjects having a heart failure, cardiac dysfunction, adverse conditions associated with heart failure, or adverse conditions as a result of having chemotherapeutic treatment, as compared to a comparable sample taken from control subjects (e.g., a person with a negative diagnosis of heart failure or a healthy subject). The term "biomarker" is used interchangeably with the term "marker."

In one embodiment, determining the gene expression profile refers to methods to assess mRNA abundance, or in another embodiment, gene product abundance. According to this aspect of the invention, and in one embodiment, gene product refers to the translated protein. In one embodiment, protein abundance reflects gene expression profiles, which may be determined, in other embodiments, by any methods known in the art, such as, but not limited to Western blot analysis, RIA, ELISA, HPLC, functional assays, such as enzymatic assays, as applicable, and others. In one embodiment, expression profile is determined by a change in mRNA levels, or in another embodiment in surface expression, or in another embodiment in secretion or in another embodiment other partitioning of a polypeptide.

In one embodiment, sustained elevations in circulating NRG-1β levels are independently associated with a subsequent increased risk of hospitalization for heart failure and cardiovascular death. In yet another embodiment, circulating NRG-1β levels are associated with progressive concentric cardiac remodeling and hypertrophy in a linear fashion in said subject.

In one embodiment, the term "independently associated" refers to an association that is not necessarily causative, for e.g., the level of expression of the biomarker does not cause the disease or adverse condition provided herein.

In one embodiment, "increased expression" refers to an increase in the level or in another embodiment, activity of target gene product relative to the level or activity of target gene product in a standard. In another embodiment, increased expression refers to between a 10 to about a 250% increase in mRNA levels, or in another embodiment, in protein levels. In another embodiment, increased expression refers to changes in gene expression at the mRNA or protein level, in terms of its pattern of expression in particular examples, such as, for example, and in one embodiment, increased expression in a biological sample. In one embodiment, increased expression is synonymous with over-expression, or stimulated expression. In another embodiment, increased expression is a relative determination, wherein expression is greater than the standard, or in cases where expression is absent in the standard, this despite expression being barely detectable in the subject. It is to be understood that any such circumstance described hereinabove, represents increased expression for the methods of this invention.

In one embodiment, "diminished expression" refers to a reduction in the level or in another embodiment, activity of target gene product relative to the level or activity of the target gene product in a standard. In one embodiment, diminished expression is synonymous with decreased expression, or in another embodiment with under-expression. In one embodiment, the expression of the gene or product is absent in the subject, or slightly less than the standard.

In one embodiment, "compared to a standard", refers to relative changes in expression where the standard is derived from a single individual, or is derived from pooled subjects who have been successfully categorized as being healthy.

In one embodiment, the term "measuring" refers to methods which include detecting the presence or absence of marker(s) in the sample, quantifying the amount of marker(s) in the sample, and/or qualifying the type of biomarker. Measuring can be accomplished by methods known in the art and those further described herein, including but not limited to SELDI and immunoassay. Any suitable methods can be used to detect and measure one or more of the markers described herein. These methods include, without limitation, mass spectrometry (e.g., laser desorption/ionization mass spectrometry), fluorescence (e.g. sandwich immunoassay), surface plasmon resonance, ellipsometry and atomic force microscopy.

In one embodiment, the phrase "differentially present" refers to differences in the quantity and/or the frequency of a marker present in a sample taken from subjects having heart failure, a cardiac dysfunction, adverse conditions associated with heart failure, or adverse cardiac conditions as a result of having chemotherapeutic treatment.

A polypeptide is differentially present between two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between two sets of samples if the frequency of detecting the polypeptide in the subjects' samples is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

In one embodiment, the term "diagnostic" refers to identifying the presence or nature of a pathologic condition, for e.g., a severity of heart failure. In one embodiment, the term "sensitivity" of a diagnostic assay refers to the percentage of diseased individuals who test positive (percent of "true positives"). Diseased individuals not detected by the assay are "false negatives." Subjects who are not diseased and who test negative in the assay, are termed "true negatives." In another embodiment, the "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., µg/ml) or a relative amount (e.g., relative intensity of signals).

A "diagnostic amount" of a marker refers to an amount of a marker in a subject's sample that is consistent with a diagnosis of a heart failure severity or an adverse cardiological condition from an unknown etiology or as a result of chemotherapeutic therapy. A diagnostic amount can be either in absolute amount (e.g., 1 µg/ml) or a relative amount (e.g., relative intensity of signals).

A "control amount" or a "standard" amount of a marker can be any amount or a range of amount, which is to be compared against a test amount of a marker. For example, a control amount of a marker can be the amount of a marker in a healthy subject. A control amount can be either in absolute amount (e.g., µg/ml) or a relative amount (e.g., relative intensity of signals).

In another embodiment, the terms biomarker and antigen are used interchangeably.

In another embodiment, the methods provided herein, comprise protein level (amount) measurements. In another embodiment, the methods provided herein, comprise DNA measurements. In another embodiment, the methods provided herein, comprise RNA measurements. In another embodiment, the methods provided herein, comprise mRNA measurements. In another embodiment, methods of measuring the expression level of a given protein used as a biomarker are known to one of average skill in the art. In another embodiment, methods of measuring the transcription level of a given RNA molecule encoding a protein used as a biomarker are known to one of average skill in the art. In another embodiment, methods of measuring the transcription level of a given mRNA molecule encoding a protein used as a biomarker are known to one of average skill in the art.

Methods for capturing, analyzing, quantifying, etc., biomarkers are know in the art, can be captured with capture reagents immobilized to a solid support, such as any biochip described herein, a multiwell microtiter plate or a resin. Once captured on a substrate, e.g., biochip or antibody, any suitable method can be used to measure a marker or markers in a sample. For example, markers can be detected and/or measured by a variety of detection methods including for example, gas phase ion spectrometry methods, optical methods, electrochemical methods, atomic force microscopy and radio frequency methods. Using these methods, one or more markers can be detected. MAP analysis represents a highly quantitative and rapid method for simultaneously analyzing a large number of specific antigens using a very small volume of patient plasma. In another embodiment, analysis of circulating antigen levels within a collected biological sample, via MAP, yields results equivalent to an ELISA assay. In another embodiment, MAP yields results with greater efficiency and with a higher throughput capacity, than an ELISA assay.

If desired, the sample can be prepared to enhance detectability of the markers. For example, to increase the detectability of markers, a blood serum sample from the subject can be fractionated by, e.g., Cibacron blue agarose chromatography and single stranded DNA affinity chromatography, anion exchange chromatography, affinity chromatography (e.g., with antibodies) and the like. The method of fractionation depends on the type of detection method used. Any method that enriches for the protein of interest can be used. Sample preparations, such as pre-fractionation protocols, are optional and may not be necessary to enhance detectability of markers depending on the methods of detection used. For example, sample preparation may be unnecessary if antibodies that specifically bind markers are used to detect the presence of markers in a sample.

Typically, sample preparation involves fractionation of the sample and collection of fractions determined to contain the biomarkers. Methods of pre-fractionation are well known to those of skill in the art and include, for example, size exclusion chromatography, mass spectrometry, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis. Examples of methods of fractionation are described in PCT/US03/00531, but are not limited to, various kinds of chromatography (e.g., anion exchange chromatography, affinity chromatography, sequential extraction, and high performance liquid chromatography) and mass spectrometry. The separation and detection of the proteins in a plasma sample generates a protein spectra for that sample.

Biomarkers in a sample can also be separated by high-resolution electrophoresis, e.g., one or two-dimensional gel electrophoresis. A fraction containing a marker can be isolated and further analyzed by gas phase ion spectrometry. In another embodiment, two-dimensional gel electrophoresis is used to generate two-dimensional array of spots of biomarkers, including one or more markers. See, e.g., Jungblut and Thiede, Mass Specir. Rev. 16:145-162 (1997).

The two-dimensional gel electrophoresis can be performed using methods known in the art. See, e.g., Deutscher ed., Methods In Enzymology vol. 182. Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in one-dimensional array are further separated using a technique generally distinct from that used in the first separation step. For example, in the second dimension, biomarkers separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomarkers. Typically, two-dimensional gel electrophoresis can separate chemically different biomarkers in the molecular mass range from 1000-200,000 Da within complex mixtures. The pI range of these gels is about 3-10 (wide range gels).

Biomarkers in the two-dimensional array can be detected using any suitable methods known in the art. For example, biomarkers in a gel can be labeled or stained (e.g., Coomassie Blue or silver staining). If gel electrophoresis generates spots that correspond to the molecular weight of one or more markers of the invention, the spot can be further analyzed by gas phase ion spectrometry. For example, spots can be excised from the gel and analyzed by gas phase ion spectrometry. Alternatively, the gel containing biomarkers can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI (e.g., using ProteinChip® array) as described herein.

Another method available for use in the present invention is gas chromatography. Prior to gas phase ion spectrometry analysis, it may be desirable to cleave biomarkers in the spot into smaller fragments using cleaving reagents, such as proteases (e.g., trypsin). The digestion of biomarkers into small fragments provides a mass fingerprint of the biomarkers in the spot, which can be used to determine the identity of markers if desired.

In one embodiment, the biological sample is analysed for the presence of the biomarker(s). In another embodiment, methods for protein analysis that are well known in the arts and are available for use in the present invention include, but are not limited to, Mass Spectrometry, Two-Dimensional Electrophoresis Chromatography High Performance Liquid Chromatography, Reversed-Phase Chromatography Ion Exchange Chromatography, and the like.

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

An immunoassay is an assay that uses an antibody to specifically bind an antigen (e.g., a marker). The immunoassay is characterized by the use of specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a marker from specific species such as rat, mouse, or human can be selected to obtain only those polyclonal antibodies that are specifically immunoreactive with that marker and not with other proteins, except for polymorphic variants and alleles of the marker. This selection may be achieved by subtracting out antibodies that cross-react with the marker molecules from other species.

In another embodiment, provided herein is a kit for diagnosing or providing prognosis for a subject developing heart failure, comprising equipment including, but not limited to, assays and analytical tools for the assays, both as described herein below in the exemplification, reagents, standards and instructions for analyzing the expression level of two or more biomarkers in a biological sample of the subject.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array described above. In one embodiment, the sample is a biological fluid sample taken from a subject. Examples of biological fluid samples include blood, serum, plasma, nipple aspirate, urine, tears, saliva etc. In another embodiment, the biological fluid comprises blood serum. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Methods for measuring the amount of, or presence of, antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltammetry and amperometry methods. Radio frequency methods include multipolar resonance spectroscopy. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Immunoassays can be used to determine presence or absence of a marker in a sample as well as the quantity of a marker in a sample. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

When the sample is measured and data is generated, e.g., by methods described herein such as, but not limited to mass spectrometry, the data is then analyzed by a computer software program. Generally, the software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" one and determines the closeness of fit between the two signals. The software also can include code indicating which the test sample is closest to, thereby providing a probable diagnosis.

In one embodiment of the present invention, multiple biomarkers are measured. The use of multiple biomarkers increases the predictive value of the test and provides greater utility in diagnosis, categorization of the severity of a subject or patient's condition, patient stratification and patient monitoring. The process called "Pattern recognition" detects the patterns formed by multiple biomarkers and greatly improves the sensitivity and specificity of clinical proteomics for predictive medicine. Subtle variations in data from clinical samples, e.g., obtained using methods provided herein and those know in the art, indicate that certain patterns of protein expression can predict phenotypes such as the presence or absence of a certain disease, a particular stage of a disease, or a positive or adverse response to drug treatments.

In one embodiment, the term "homology" or "homologous" refers to a protein from another organism when the encoded amino acid sequence of the protein has a similar sequence to the encoded amino acid sequence of a protein from a different organism and in another embodiment, has a similar biological activity or in another embodiment, similar function. In one embodiment, a protein may have homology or be homologous to another protein if the two proteins have similar amino acid sequences and have similar biological activities or functions. In another embodiment, "homologous" does not necessarily imply that there is an evolutionary relationship between the proteins. In one embodiment, the term "homologous" refers to that the two proteins have similar amino acid sequences and similar biological activities or functions. In one embodiment, a homologous protein exhibits 50% sequence similarity to the wild type protein, or in another embodiment 60% sequence similarity, or in another embodiment 70% sequence similarity. or in another embodiment 80%, 85% or 90% sequence similarity to the wild type protein. or in another embodiment, a homologous protein exhibits 95%, 97%, 98% or 99% sequence similarity.

In one embodiment, the methods of the invention provide for the use of multiple assays, to evaluate differential gene expression. In another embodiment, arrays are used since microarray analysis allows in another embodiment simultaneous gene expression analysis of multiple genes in a high-throughput mode.

In one embodiment, a combination of biomarkers may provide greater predictive value than single markers alone. In another embodiment, the detection of a plurality of markers in a sample increases the percentage of true positive and true negative diagnoses and would decrease the percentage of false positive or false negative diagnoses. Thus, and in one embodiment, the methods of the present invention comprise the measurement of more than one biomarker.

In other embodiments, the measurement of markers can involve quantifying the markers to correlate the detection of markers with a probable diagnosis of the severity of heart failure, regardless of the cause of the heart failure, for e.g. such as when it's cause is as a result of chemotherapeutic treatment. Thus, if the amount of the markers detected in a subject being tested is different compared to a control amount (i.e., higher or lower than the control, depending on the marker), then the subject can be classified as having a certain risk of heart failure.

The correlation may take into account the amount of the marker or markers in the sample compared to a control amount of the marker or markers (up or down regulation of the marker or markers) (e.g., in normal healthy subjects). A control can be, e.g., the average or median amount of marker present in comparable samples of healthy subjects. The control amount is measured under the same or substantially similar experimental conditions as in measuring the test amount. The correlation may take into account the presence or absence of the markers in a test sample and the frequency of detection of the same markers in a control. The correlation may take into account both of such factors to facilitate determining/practicing the methods provided herein.

In another embodiment, a suitable statistical tool, known to one of skill in the art, is used to determine whether or not a biomarker is over-expressed or under-expressed relative to a standard.

In one embodiment, continuous measures such as NRG-1β are described using simple statistics (mean, median, standard deviation, and range) and categorical/ordinal data (e.g. race, gender, and remodeling geometry) with tables and frequencies.

In another embodiment, graphical methods including histograms, scatter plots, and box plots are used to understand aspects of data quality and examine assumptions that underlie parametric and semi-parametric models.

In one embodiment, to better understand the changes in exposure and outcome over time, individual trajectories are plotted as well as group summaries across time, and Kaplan-Meier plots are used to estimate survival probabilities.

In one embodiment the methods provided herein further comprise managing subject treatment based on the status. Such management describes the actions of the physician or clinician subsequent to determining the severity of heart failure. For example, if the result of the methods of the present invention is inconclusive or there is reason that confirmation of status is necessary, the physician may order more tests. Alternatively, if the status indicates that treatment is appropriate, the physician may schedule the patient for treatment. Likewise, if the result is negative, e.g., the status indicates no need for heart failure treatment is needed, no further action may be warranted. Furthermore, if the results show that treatment has been successful, no further management may be necessary.

The invention also provides for such methods where the biomarkers (or specific combination of biomarkers) are measured again after subject management. In these cases, the methods are used to monitor the status of the severity of heart failure or cardiac dysfunction in a subject. Because of the ease of use of the methods and the lack of invasiveness of the methods, the methods can be repeated after each treatment the patient receives. This allows the physician to follow the effectiveness of the course of treatment. If the results show that the treatment is not effective, the course of treatment can be altered accordingly. This enables the physician to be flexible in the treatment options.

In another example, the methods for detecting markers can be used to assay for and to identify compounds that modulate expression of these markers in vivo or in vitro.

In yet another embodiment, the markers are used in heredity studies to determine if the subject is at risk for developing a more severe case of heart failure.

"Solid support" refers to a solid material which can be derivatized with, or otherwise attached to, a capture reagent. Exemplary solid supports include probes, microtiter plates and chromatographic resins.

"Probe" in the context of this invention refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A "probe" will generally comprise a solid substrate (either flexible or rigid) comprising a sample presenting surface on which an analyte is presented to the source of ionizing energy.

"Eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Analyte" refers to any component of a sample that is desired to be detected. The term can refer to a single component or a plurality of components in the sample.

The "complexity" of a sample adsorbed to an adsorption surface of an affinity capture probe means the number of different protein species that are adsorbed. "Monitoring" refers to recording changes in a continuously varying parameter.

In one embodiment, provided herein is a kit comprising reagents for detecting the gene expression profile, wherein the reagents are nucleic acids, which may hybridize to mRNA isolated from a biological sample. In one embodiment, reagents may be labelled, or in another embodiment nucleic acids isolated from a biological sample are labelled. In another embodiment, the kit provides instructions for detecting the label qualitatively in another embodiment, quantitatively.

In another embodiment the kit further comprises a buffering agent, or in another embodiment, a preservative, or in another embodiment a protein stabilizing agent. In one embodiment, the kit further comprises an enzyme or a substrate. In one embodiment, the substrate may be a means of detecting a label, or in another embodiment the expressed protein product itself. In one embodiment, the kit further comprises reagents that are necessary for detection of nucleic acids, amino acids or hybridization signals for nucleic acids.

In one embodiment, detecting differential expression of the genes via the kits of the invention is accomplished using established PCR, ELISA, RIA, and other similarly recognized methods, and the reagents comprise those appropriate for the particular assay for detection.

In one embodiment, the results obtained are compared to a standard, which, in another embodiment, may comprise a series of standards, which, in another embodiment is used in the kits of the invention for quantification of differential expression. In one embodiment, the standard may comprise any embodiment listed herein, and in another embodiment, will be suitable for a particular application of the kit. In one embodiment, the standard comprises nucleic acids when the kit is used for the determination of nucleic acid profile, or in another embodiment the standard is a protein when the kit is used for the determination of expressed protein profile.

In one embodiment, the kit may be adapted for high-throughput screening, and comprise a microarray.

In one embodiment, the kit further comprise agents, which in another embodiment may comprise antibodies, or other agents which detect activity or in another embodiment expression of the translated protein product. In one embodiment the agents comprise antibodies that detect the presence of specific nucleic acids.

In one embodiment, the kit comprises a microarray, which comprises cRNA of the genes indicated, and others. In one embodiment, the kit may comprise standard oligonucleotide probes, PCR reagents and detectable labels. In another embodiment, the kit may comprise biological samples taken from human subjects. The standard will comprise all embodiments listed herein for the standard, including in one embodiment nucleic acid from pooled samples as provided herein.

In one embodiment the kits of the invention evaluate multiple genes, and in another embodiment help in the generation of a gene expression profile, which is useful in the methods of this invention.

In one embodiment, the kit further comprises a positive and negative control, wherein said standards can be assayed and compared to the test sample.

In one embodiment, the kit may further comprise labeled cDNA. Fluorescently labeled cDNA probes may be generated through incorporation of fluorescent nucleotides by reverse transcription of RNA extracted from samples of interest Such methods have been shown to have the sensitivity required to detect rare transcripts, which are expressed at a few copies per cell, and to reproducibly detect at least approximately two-fold differences in the expression.

In one embodiment, the methods of this invention employ probes and primers, which may include repetitive stretches of adenine nucleotides (poly-A tails) normally attached at the ends of the RNA, for the identification of differentially expressed genes. In another embodiment, kits of this invention may comprise such probes.

In one embodiment, the biomarker is a functional biomarker or a functional fragment thereof. In another embodiment, the biomarker is a functional variant or fragment thereof of a biomarker provided herein. In another embodiment the biomarker is a homolog of a biomarker provided herein, where in another embodiment, it is a paralog or an ortholog of a biomarker provided herein.

In one embodiment, cRNA refers to complementary ribonucleic acid or substantially complementary ribonucleic acid. In another embodiment, cRNA refers to the hybridization or base pairing between nucleotides or nucleic acids, such as, for instance, between the two strands RNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair in one embodiment, with at least about 70% of the nucleotides of the other strand, or in another embodiment with about 90% to 95%, and in another embodiment with about 98 to 100%.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to inducing remission. In another embodiment, "treating" refers to slowing the progression of a disease. The terms "reducing", "suppressing"

and "inhibiting" refer in another embodiment to lessening or decreasing. Each possibility represents a separate embodiment of the present invention.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequalae. The term "subject" does not exclude an individual that is normal in all respects. In another embodiment, the term encompasses "patient" is encompassed within the term "subject".

The following examples are presented in order to more fully illustrate the preferred embodiments of the invention. They should in no way be construed, however, as limiting the broad scope of the invention.

EXAMPLES

Study Population and Study Design

To define the role of NRG-1β in human cardiac remodeling and the risk of adverse cardiovascular events, we have engaged in a comprehensive study of NRG-1β in PHFS and CRIC subjects (which together represent the entire spectrum of remodeling); an efficient study design (FIG. 2); a reproducible neuregulin assay; rich datasets with both clinical and echocardiographic outcomes; and an experienced, collaborative team of mentors. Studies in PHFS and studies in CRIC nested case-cohorts define the relationship between NRG-1β and risk of future clinical outcomes. Studies in CRIC define the relationship between NRG-1β and cardiac remodeling.

The Penn Heart Failure Study (PHFS) is an ongoing prospective cohort study of outpatients with chronic heart failure recruited from the Penn Heart Failure and Transplantation program. The primary inclusion criterion is a clinical diagnosis of heart failure, and the cohort is comprised of patients with a broad spectrum of disease. Participants are excluded if they have a noncardiac condition resulting in an expected mortality of less than 6 months, as judged by the treating physician.

At time of study entry, detailed clinical data were obtained using questionnaires administered to the patient and treating physician, with verification via medical records. Variables such as NYHA Class and cardiomyopathy etiology (ischemic versus nonischemic) were determined by the physician based upon all available clinical data and according to standard heart failure clinical practice guidelines. Venous blood samples were obtained at enrollment and stored at $-80°$ C. In this cohort, approximately 68% of the subjects are male, with an overall mean age of 56 years. The cohort is 83% Caucasian and 15% African Americans. There is a predominance of eccentric hypertrophy, and the mean ejection fraction is approximately 32% with primarily NYHA Class II/III and ACC/AHA Heart Failure Stage C subjects (Table 1). Cardiomyopathy etiologies include: 32% ischemic, with the remainder of nonischemic cardiomyopathies (68%) primarily distributed among idiopathic (37%), hypertensive (9%), valvular (4.8%), congenital (2.3%), and familial (2%). Nearly 56% of the subjects have had at least 1 cardiac hospitalization since enrollment. The percentage of deaths and transplants to date are each on the order of 10.3-11.9% over a median follow-up of 2.4 years.

Two-dimensional transthoracic echocardiography with Doppler color flow imaging was performed in all patients at an ICAEL-accredited laboratory within approximately 30 days of blood sampling. Echocardiograms were performed by an experienced sonographer and clinical interpretation performed by a Level III-certified echocardiographer, with all personnel blinded to NRG-1β levels. Ejection fraction (EF) was visually estimated by the expert reader, according to standard clinical protocol.

Follow-up events including all-cause mortality and cardiac transplantation were prospectively ascertained every 6 months via direct patient contact and verified through death certificates, medical records, and contact with patients' family members.

All participants provided written, informed consent, and the PHFS protocol was approved by our Institutional Review Board.

Confounders are factors that are associated with the exposure, and independent of the exposure, are a risk factor for the outcome of interest. A confounder can alter the true association between exposure and outcome. Factors that are known to be associated with both the outcomes and exposure are evaluated. Below is a description of potential confounders.

Demographic variables such as age, sex, and race have all been associated with clinical outcomes in subjects with eccentric remodeling. Age is treated both as a continuous variable and categorized according to 10-year increments to explore for nonlinearity. Tobacco use is considered as a potential confounder, and will be classified as current, former, and never. Medication use including ace-inhibitors, angiotensin receptor blockers, beta-blockers, digoxin, hydralazine/nitrates, and diuretics are assessed as a binary covariate (yes/no). Device therapy such as cardiac resynchronization are assessed as a confounder given the beneficial effects of biventricular pacing in decreasing rate of hospitalization and improving survival. Heart failure etiology (ischemic versus nonischemic) and severity (NYHA Class) are considered confounders because survival differences exist according to primary cause of disease and degree of symptomatology. Comorbidities such as history of renal disease (creatinine and glomerular filtration rate as a continuous and categorical variable), hypertension, diabetes (comorbidities will be assessed as yes/no), and atrial arrhythmia history are considered given our univariate, cross-sectional findings. Duration of heart failure diagnosis is also assessed as a potential confounder. Both the patient's report of heart failure diagnosis and date of first cardiac hospitalization prior to study enrollment. In addition, a measure of cardiac remodeling and function, such as ventricular mass or ejection fraction is included as a potential confounder, given its relationship with survival. In our multivariable analysis, possible confounding by BNP is also assessed, given its associations with cardiac mortality and morbidity in subjects with heart failure and potential relationship with exposure, secondary to neurohormonal effects. BNP is treated as continuous and categorical. Additional potential confounders include exercise capacity, body mass index, and factors related to increased strain, such as blood pressure, and neurohormonal status.

In the $2^{nd}$ study (CRIC), the cross-sectional and longitudinal associations between changes in NRG-1β levels and cardiac remodeling in a random sample of the entire CRIC cohort is assessed. The effects of NRG-1β plasma levels at years 1, 2, 3, and 4 are assessed and results are related to echocardiography data obtained at years 1 and 4. The exposure is circulating NRG-1β level and the primary outcomes are changes in relative wall thickness (RWT) and left ventricle (LV) internal diameter at end-diastole (LVIDd) are indexed to BSA. Additional secondary outcomes include changes in indexed LV mass, LV end-diastolic volumes (LV EDV), LV indexed end-systolic (LV ESV), LV internal diameter at end-systole (LVIDs), and ejection fraction (EF). All of these outcomes are quantified as part of the core lab interpretation of echoes in CRIC. The following specific analyses, are stratified according to remodeling geometry (normal, concentric remodeling, concentric hypertrophy, and eccentric hypertrophy), given that the relationship between NRG-1β and remodeling may differ by strata.

The cross-sectional association between NRG-1β at Year 1 and echo parameters of ventricular remodeling and function at Year 1 are defined using linear regression. Subjects are stratified based upon NRG-1β level and it is determined if significant differences in echocardiographic parameters of remodeling exist across each ordered strata. The shape of the NRG-1β time relationship is assessed according to cardiac geometry.

The baseline or temporal changes in NRG-1β levels predict the change in echocardiographic parameters of ventricular remodeling and function over years 1 and 4. As a first step, it is determined if NRG-1β levels at Year 1 predict change in remodeling. Next, the temporal changes in NRG-1β are assessed. If the pattern appears linear, the following two-stage analysis is performed: a linear model is fitted to the four NRG-1β data points at Years 1 through 4 to estimate the annual rate of change in NRG-1β for each subject. This annual rate of change in NRG-1β as a predictor of change in echocardiography parameters. The change in echocardiography parameters are assessed for normality and log transformed when appropriate. If changes in NRG-1β are nonlinear over time, multiple indicator variables of change (e.g. year 1 versus year 2, year 1 versus year 3, and so forth or a summary of these changes such as median or maximum change) are used to determine whether there are periods when changes in NRG-1β levels are critical to the subsequent outcomes. A simple average of the 4 levels of NRG-1β, is used after considering the distribution of NRG-1β over time.

For the $2^{nd}$ and $3^{rd}$ studies in CRIC (see FIG. 2), a similar list of confounders as described above in PHFS is used. Here, the degree of renal dysfunction is considered since it is known to be related to echocardiographic parameters of ventricular remodeling. Stratifying our analyses according to ventricular geometry will help control for the varying degrees of renal dysfunction between the 4 types of remodeling geometry given the association between geometry and renal function. Renal function using glomerular filtration rate (GFR) as measured in CRIC are estimated by the modified simplified MDRD equation (GFR ml/min per 1.73 $m^2$=186×[serum Cr (mg/dl)]$^{-1.154}$×[age]$^{-0.203}$×[0.742 if female]×[1.212 if African American]), using locally measured serum creatinine calibrated to a central laboratory. Overall, those variables that have a univariate association with our outcome of interest at an α of less than 0.20 are chosen. Model fit is explored using residuals and compared using adjusted $R^2$.

The change in NRG-1β over time and change in remodeling geometry at year 4 for subjects with normal geometry at year 1, and the change in remodeling geometry at year 4 for subjects with concentric hypertrophy/remodeling at year 1, will be estimated. The generalized estimating equations (GEE) are used to determine if, among those with normal geometry at year 1, an increase in circulating NRG-1β over time is associated with a change in remodeling geometry from normal to concentric remodeling/hypertrophy at year 4. GEE is used to determine if, among those with concentric remodeling/hypertrophy and remodeling at year 1, changes in circulating NRG-1β over time differ between those with concentric and eccentric hypertrophy at year 4. This will involve the addition of an interaction term, remodeling geometry, in our model.

Analyses are stratified based upon normal geometry, concentric remodeling, concentric hypertrophy, and eccentric hypertrophy, given that remodeling geometry is an effect modifier. In the secondary analyses, GFR, blood pressure, and anti-hypertensive medication are considered as potential effect modifiers.

In the $3^{rd}$ study which also involves CRIC (see FIG. 3) the longitudinal association between NRG-1β levels and combined time-to-event outcomes including first heart failure hospitalization and cardiac death is assessed using a case-cohort design.

The sampling scheme for the case-cohort study induces a correlation between subjects in both groups that must be taken into account in the analyses. The basic principle behind the solution to this problem is that a case outside the subcohort is considered to not be at risk until just before the failure, and is thus not included in earlier risk sets. This is accomplished using a weighting term, of which three have been reported in the literature, namely the Prentice, Self and Prentice, and Barlow methods. The Self and Prentice method in STATA 10.0 are used for our analysis, as this weighting scheme has been evaluated in simulation studies and is a valid and powerful method for analyzing these data. The specific analytic plans for the $3^{rd}$ study (clinical outcomes study in CRIC) are as follows: A) Describe the association between NRG-1β levels at year 1 and the primary outcomes time-to-cardiac death and first heart failure hospitalization via Kaplan-Meier plots and median survival time estimates. B) Assess the univariate association between NRG-1β levels at year 1 and primary outcomes via weighted Cox proportional hazards methods as described above. C) Determine whether NRG-1β levels at year 1 are an independent risk factor for the primary outcomes after adjustment for clinical risk factors, again using weighted Cox models. Potential confounders are similar to that described above for study 1 in PHFS and study 2 in CRIC. These include age (continuous, categorical), sex, race, tobacco (current, former, never), ventricular mass, renal dysfunction, history of coronary disease, hypertension, diabetes, atrial arrhythmia, and anti-hypertensive medication. From the list of potential confounders, those variables that lead to a 10% change in the estimate of the association between NRG-1β and the HR are selected for the outcomes of interest. D) Determine whether temporal changes in NRG-1β are associated with survival. In this two-step analysis, a linear model is used to construct an estimate of the rate of change in NRG-1β for each subject, and then this estimate is used as a predictor of survival. In addition to including NRG-1β as a linear term in the model, it is assessed whether more complicated patterns of change in NRG-1β are predictive of survival given that the relationship may be nonlinear. Different indicator variables of change corresponding to the change from year 1 NRG-1β (e.g. year 1 versus year 2, year 1 versus year 3, and so forth or a summary of these changes such as median or maximum change) are included. A simple average of the 4 levels of NRG-1β, are used after considering the distribution of NRG-1β over time. Covariates detailed as potential confounders as above are introduced. E) As part of our secondary analyses, the effect modification by remodeling geometry is assessed by introducing a product term in our multivariable Cox models. Ischemic versus nonischemic etiology of heart failure is considered as a potential effect modifier based upon our PHFS findings. Heart failure severity is not as relevant given only NYHA I/II subjects are included in CRIC. Effect modification by renal dysfunction, is assessed by GFR; hypertension; and common anti-hypertensive therapies will also be explored.

Sample Size and Power

All calculations assume 80% power with a type 1 error rate of 0.05, and two-sided test. The proposed sample size requirements are summarized in Table 1, and the methods to obtain these estimates are detailed below:

TABLE 1

Summary of Sample Size Requirements Assuming 80% Power

| Study | Study Design | Remodeling Geometry | Proposed Sample Size |
|---|---|---|---|
| 1 | PHFS Subcohort | Eccentric hypertrophy | 1800 (≥600 per stratum) |
| 2 | CRIC Subcohort | Normal, Concentric Remodeling, Concentric Hypertrophy, and Eccentric Hypertrophy (All) | 800 (200 per remodeling geometry) |
| 3 | CRIC Case-Cohort | Normal, Concentric Remodeling, Concentric Hypertrophy, and Eccentric Hypertrophy (All) | 361 cases, 800 subcohort (total of 1081 subjects) |

For Study 1 in PHFS, a conservative event rate of approximately 15% (transplant or death) or 50% (incident cardiac hospitalization) is assumed based upon the number of events to date. For the entire cohort of 1800 subjects with eccentric hypertrophy there will be 80% power to detect a HR of 1.31 for the combined endpoint of death or transplant and 1.18 for incident cardiac hospitalization (Table 2), assuming patients are divided by median NRG-1β level. In our primary stratified analyses, we expect subgroups by heart failure etiology to be no smaller than 600 subjects. The detectable HR for transplant-free survival are thus on the order of 1.56 for subgroups stratified by etiology. A similar calculation suggests a HR of 1.32 for first cardiac hospitalization. By severity, no subgroup is expected to be smaller than 800 subjects, which yields a detectable HR of 1.48 for transplant-free survival and 1.27 for incident hospitalization. These detectable HRs are all consistent with the HRs suggested by our pilot data. These sample size estimates based upon subgroup analyses also provide an approximation of the detectable HR with a potential interaction, given the effect size will be in the same range as at least one of the strata.

TABLE 2

Detectable Hazard Ratios by Median NRG-1β for Event Rates of 15% and 50% with 80% Power in PHFS.

| Event Rate | Sample Size | HR |
|---|---|---|
| 15% | 200 | 2.07 |
| 15% | 400 | 1.71 |
| 15% | 600 | 1.56 |
| 15% | 800 | 1.48 |
| 15% | 1200 | 1.38 |
| 15% | 1800 | 1.31 |
| 50% | 200 | 1.60 |
| 50% | 400 | 1.40 |
| 50% | 600 | 1.32 |
| 50% | 800 | 1.27 |
| 50% | 1200 | 1.22 |
| 50% | 1800 | 1.18 |

The sample size for Study 2 in CRIC is fixed based upon Study 3 (which drives the overall sample size requirements for the CRIC-based portion). Based on these latter estimates, which are detailed below, there will be approximately 170 subjects in each stratum of remodeling geometry given the distribution of remodeling geometry as shown in Table 3 (200 subjects with, at a minimum, quantifiable echo results in 85%). Assuming a linear regression model, where change in echocardiographic parameter is the dependent variable and change in NRG-1β is the independent variable, 170 subjects would give us a detectable regression coefficient (β) of 0.25 for LVIDd and 0.08 for PWT. This translates to a very small coefficient of determination ($R^2$) of 0.04 in each stratum. If we had a smaller number of subjects in each stratum (e.g. 100), we would still be able to detect an $R^2$ of 0.07.

TABLE 3

Remodeling Geometry in cohort

| Remodeling Geometry | Percent of cohort |
|---|---|
| Normal | 28.6% |
| Concentric Remodeling | 19.8% |
| Concentric Hypertrophy | 29.3% |
| Eccentric Hypertrophy | 22.2% |

For Study 3 in CRIC, a case-cohort study, based upon initial data, there have been approximately 322 deaths to date (of 3612 subjects at baseline and 7,450 person years). In terms of heart failure hospitalizations, 3.1% of the cohort has experienced a hospitalization during year 0-1 of follow-up; 3.6% during year 1-2; 2.6% during year 2-3; and 3.4% during year 3-4. Note that these estimates for both death and heart failure hospitalizations do not include all the events that will have occurred after Year 1 of enrollment, as follow-up is ongoing. Table 4 demonstrates our detectable hazard ratios (HR) assuming that the cohort is divided by median NRG-1β level, estimate event rates of 3% (death only) and 10% (combined), and use an alpha of 0.05. In order to maximize efficiency, a subcohort of 800 subjects is sampled as this provides a reasonable detectable HR for death only (HR 1.76) and the combined endpoint of death and heart failure hospitalization (HR 1.41).

TABLE 4

Detectable Hazard Ratios for Event Rates of 3% and 10% with 80% Power in CRIC

| Event Rate | Sample Size Subcohort | Cases | Total | HR |
|---|---|---|---|---|
| 3% | 200 | 108 | 1.94 | 1.94 |
| 3% | 400 | 108 | 1.82 | 1.82 |
| 3% | 600 | 108 | 1.78 | 1.78 |
| 3% | 800 | 108 | 1.76 | 1.76 |
| 10% | 200 | 361 | 1.87 | 1.87 |
| 10% | 400 | 361 | 1.49 | 1.49 |
| 10% | 600 | 361 | 1.43 | 1.43 |
| 10% | 800 | 361 | 1.41 | 1.41 |

NRG-1β Assay

NRG-1β is measured from frozen, previously unthawed serum or plasma samples that had been stored at −80° C. until time of assay. An indirect sandwich enzyme-linked immunosorbent assay (ELISA) was used (NRG1-β1 Duoset ELISA development system from R&D Systems, Minneapolis, Minn.). Assay technology was adapted for human samples, and all measurements were performed at Vanderbilt University. Serum or plasma was applied to plates that had been coated with mouse anti-human NRG1-β1 capture antibody. Following incubation, a biotinylated goat anti-human NRG1-β1 detection antibody was added to each well, and a streptavidin-HRP system was used for detection. The monoclonal antibody used in this assay detects a biologically active NRG-1β peptide fragment that is highly expressed in the cardiovascular system, and that activates the ErbB receptor and downstream signaling pathways in ventricular myocytes in vitro. Extensive validation was performed and there was no cross-reactivity with NRG-1α isoform or epidermal growth factor.

In PHFS, all samples were measured in duplicate, and the average of two values was used for analysis. The average intra-assay coefficient of variation (CV) was 5.6%, and the average inter-assay CV was 13%. The detection limits of the assay were 0.30 to 30 ng/ml. Samples below the detectable limit (n=13) were assigned a value halfway between 0 and the lowest detectable limit of 0.30 ng/ml (0.15 ng/ml). Samples above the detectable limit at a 1:3 dilution (n=18) were assigned a value of 30 ng/ml.

BNP Assay (in PHFS)

In PHFS, the Architect™ BNP immunoassay from Abbott Diagnostics (Abbott Park, Ill.) was used to quantify BNP in peripheral plasma in the first 744 patients enrolled. The intra- and inter-assay CVs were 0.9 to 5.6% and 1.7 to 6.7%, respectively. The lower limit of detection of BNP was 10 pg/ml.

Statistical Analysis (in PHFS; Examples 2-6)

The distribution of NRG-1β was skewed, and the natural log-transformation of NRG-1β [Ln(NRG-1β)] approximated a normal distribution. To determine cross-sectional associations between NRG-1β and clinical variables at time of study entry, linear regression was used with Ln(NRG-1β) modeled as the continuous, dependent variable. To determine the association between baseline NRG-1β level and risk of death or transplantation, Kaplan-Meier analysis and Cox proportional hazards models were used. Univariate models were constructed with NRG-1β as the predictor variable and time to all-cause death or cardiac transplantation as the combined outcome. Hazard ratios (HR) were determined for the $4^{th}$ versus $1^{st}$ quartile of NRG-1β, and for each unit increase in Ln(NRG-1β) modeled continuously. Assuming an α of 0.05 and event rate of 15%, 900 patients provided 80% power to detect a hazard ratio (HR) of 1.22 for each unit increment in Ln(NRG-1β).

For multivariable models, confounders were selected using clinical judgment, cross-sectional associations with NRG-1β, and statistical evidence of potential confounding. Statistical evidence included a univariate association with death/transplant at a p<0.20 or a change in the HR between NRG-1β and death/transplant by at least 10% after inclusion of the covariate in the model. Models were built in a sequential fashion with the addition of covariates by 1) demographics; 2) cross-sectional associations with NRG-1β (tobacco use, atrial fibrillation, bundle branch block, cardiomyopathy etiology); and 3) both statistical evidence and clinical judgment (body mass index, medication use, device therapy, and plasma BNP). The backwards elimination method was used to assess for additional confounding. Echocardiographic parameters of ventricular function were not to adjusted given that, based upon biologic data, changes in ventricular function may mediate the association between NRG-1β and risk of adverse outcomes.

The role of NRG-1β might differ according to heart failure etiology and severity of disease. Interaction terms between Ln(NRG-1β) and heart failure etiology (ischemic versus nonischemic) and between Ln(NRG-1β) and NYHA Class (I/II versus III/IV) were added into our models. To explore the joint effects of NRG-1β and BNP, patients were divided into subgroups according to their median NRG-1β and BNP levels. Cox proportional hazards ratios were computed for each of the four groups, with the reference group being NRG-1β and BNP less than the median. These analyses were stratified by heart failure etiology and NYHA Class. All analyses were performed using STATA 10.0.

Example 1

Study Population in the Penn Heart Failure Study

Between December 2003 and October 2007, 899 subjects were enrolled with a frozen blood sample available for analysis. The mean±sd age was 56±14 years, 68% were male, and 81% were Caucasian (Table 5). Patients suffered primarily from systolic heart failure, with a mean EF of 31±17 percent. The full spectrum of NYHA Class was represented, with the majority being NYHA Class II or III. One-third of patients had ischemic cardiomyopathy and the remaining two-thirds had nonischemic cardiomyopathy. The mean±sd NRG-1β was 7.0±5.9 ng/ml and the median (IQR) was 5.2 (3.4, 8.6) ng/ml.

TABLE 5

Characteristics of the study population*

| Characteristic | Entire cohort (n = 899) |
|---|---|
| Age, years | 56 ± 14 |
| Male gender | 612 (68) |
| Race | |
| Caucasian | 725 (81) |
| African American | 127 (14) |
| Other | 32 (4) |
| Tobacco use | |
| Never | 348 (39) |
| Former | 492 (55) |
| Current | 59 (6) |
| Hypertension | 320 (36) |
| Diabetes mellitus | 209 (23) |
| Serum creatinine, mg/dL | 1.3 ± 0.7 |
| Body mass index, kg/m2 | 29 ± 6.6 |
| Systolic blood pressure, mmHg | 113 ± 18 |
| Cardiomyopathy etiology | |
| Ischemic | 293 (33) |
| Nonischemic | 606 (67) |
| NYHA Class | |
| I | 134 (15) |
| II | 388 (43) |
| III | 267 (30) |
| IV | 110 (12) |
| Ejection Fraction, percent | 32 ± 17 |
| Bundle Branch Block | |
| Neither | 742 (82) |
| Left BBB | 98 (11) |
| Right BBB | 59 (7) |
| Atrial Fibrillation/Flutter | 307 (35) |
| Ventricular Tachycardia | 254 (28) |
| Cardiac resynchronization | 249 (28) |
| Ace-inhibitor or ARB | 768 (85) |
| Beta blocker | 749 (83) |
| Digoxin | 417 (46) |
| Diuretic | 637 (71) |
| Serum NRG-1β, ng/ml | |
| Median (IQR) | 5.2 (3.4, 8.6) |
| Mean ± sd | 7.0 ± 5.9 |
| Plasma BNP, pg/ml (n = 744) | |
| Median (IQR) | 120 (35, 384) |
| Mean ± sd | 322 ± 507 |

*Data are displayed as mean ± sd or frequency (percent), unless otherwise indicated

Example 2

Figure 3:
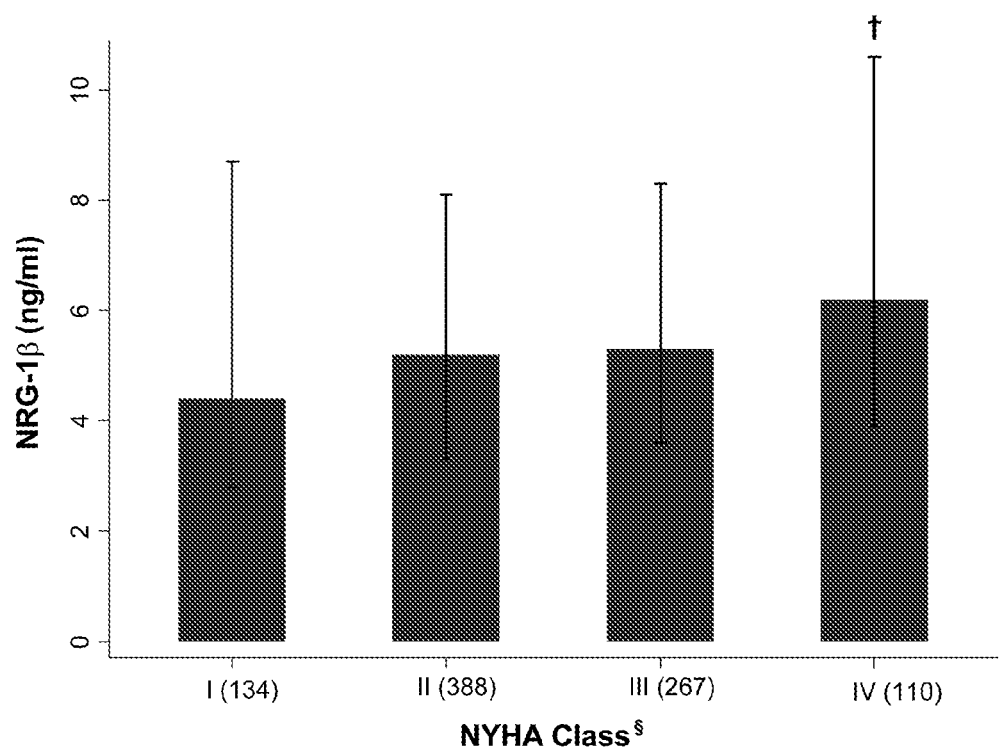
FIG. 3. Shows the median NRG-1β according to NYHA class in the Penn Heart Failure Study. Bars represent 25th and 75th percentiles. †$p<0.01$ for NYHA Class IV compared to I ($p=0.01$ overall). §Numbers in each class displayed in parentheses.

Cross-Sectional Associations Between Neuregulin-1β and Clinical Parameters in the Penn Heart Failure Study As shown in FIG. 3, NYHA Class was significantly associated with NRG-1β (overall p=0.01), with higher NRG-1β levels associated with more advanced symptom severity (NYHA Class IV median [IQR] 6.2 ng/ml [3.9, 10.6] versus Class I median 4.4 ng/ml [2.8, 8.7], p=0.002). NRG-1β was also associated with a history of atrial fibrillation/flutter, presence of left bundle branch block, cardiomyopathy etiology, and tobacco use. These covariates were treated as potential confounders in multivariable models.

Example 3

Figure 4:
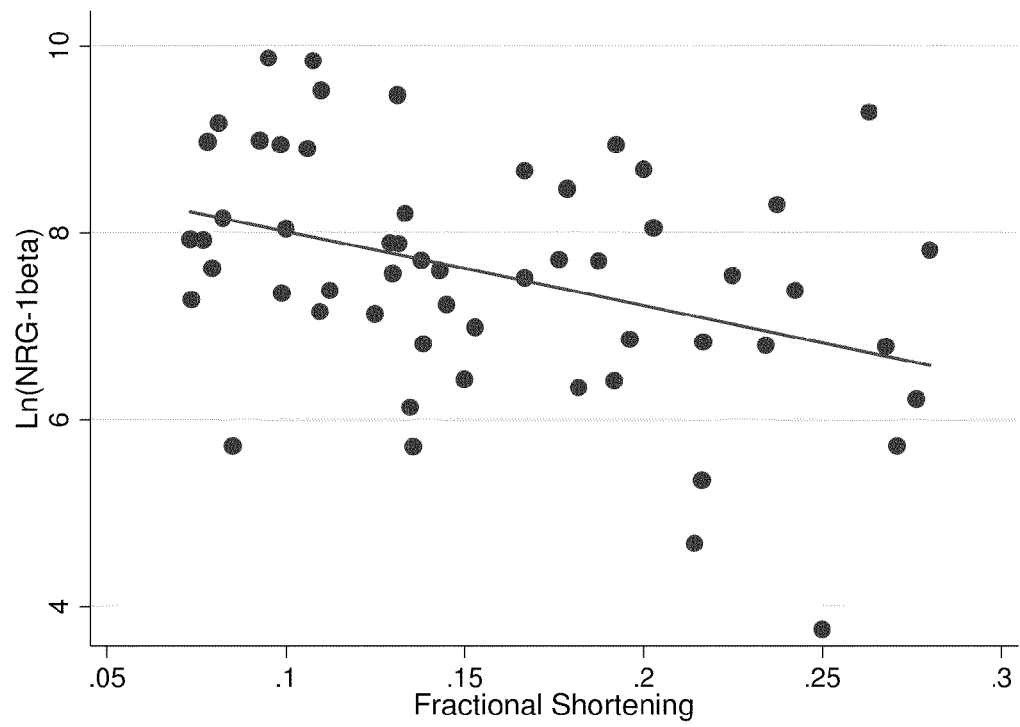
FIG. 4. Shows the relationship between Circulating NRG-1β Levels and Fractional Shortening in a subcohort of the Penn Heart Failure Study (n=56). A significant association between endocardial fractional shortening (FS) was observed, as determined by echocardiography and NRG-1β level among those with reduced cardiac function. In the group of subjects with a FS of less than 30% (n=56), there was a significant inverse relationship between the Ln(NRG-1β and fractional shortening ($\beta=-7.94$, $R^2=0.14$, $p=0.004$).

Association Between Circulating NRG-1β Levels and Cardiac Function in the Penn Heart Failure Study In prior analyses, there was also a significant association between endocardial fractional shortening (FS) as determined by echocardiography and NRG-1β level among those with reduced cardiac function. In the group of subjects with a FS of less than 30% (n=56), there was a significant inverse relationship between the Ln(NRG-1β, and fractional shortening ($\beta=-7.94$, $R^2=0.14$, p=0.004) (FIG. 4).

Example 4

Figure 5:
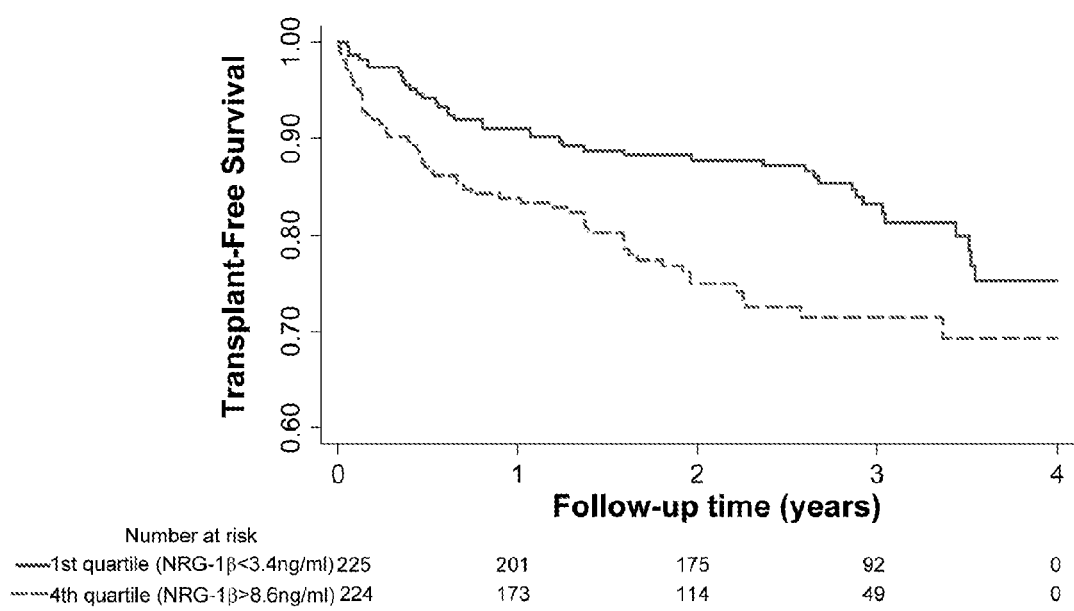
FIG. 5. Shows transplant-free survival by NRG-1β quartiles in the Penn Heart Failure Study (4th versus 1st). $p=0.03$ by the log-rank test.

Association Between NRG-1β and Risk of all-Cause Death or Cardiac Transplant in the Penn Heart Failure Study There were 192 outcomes (103 deaths and 89 transplants) over a median follow-up of 2.4 years. Patients in the highest quartile of NRG-1β (NRG-1β>8.6 ng/ml, n=224) compared to those in the lowest quartile (NRG-1β<3.4 ng/ml, n=225) had a significantly increased risk of death or transplant FIG. 5.

In Cox models (Table 6), the unadjusted hazard ratio in the highest versus lowest NRG-1β quartile was 1.75 (95% CI 1.17-2.63, p=0.007). After adjusting for demographics, this association between NRG-1β and risk of death or transplant remained significant (Table 6, Model 1). With the addition of covariates associated with NRG-1β from our cross-sectional analyses (Model 2), there were minimal changes in the relative hazard (HR 1.63, 1.08-2.47, p=0.02). Furthermore, in fully adjusted models (Models 3 and 4) that included additional potential confounders (medications, cardiac resynchronization therapy, and BNP), significance was retained. No single covariate changed the univariate HR between NRG-1β and death/transplant by more than 10%, and the backwards elimination method did not reveal further evidence of confounding. Thus, circulating NRG-1β was an independent predictor of adverse clinical outcomes in our study population.

TABLE 6

Associations between NRG-1β and risk of death or cardiac transplantation.

| | Covariates | HR (95% CI)* $4^{th}$ versus $1^{st}$ quartile of NRG-1β | P-value |
|---|---|---|---|
| Unadjusted (n = 897) | None | 1.75 (1.17-2.63) | 0.007 |
| Model 1 (n = 881) | Age, gender, race | 1.73 (1.15-2.61) | 0.008 |
| Model 2 (n = 864) | Model 1 & cardiomyopathy etiology, history of atrial fibrillation/flutter, bundle branch block, tobacco use | 1.63 (1.08-2.47) | 0.02 |
| Model 3 (n = 864) | Model 2 & body mass index, ace-inhibitor or angiotensin-receptor blocker use, beta-blocker use, and cardiac resynchronization therapy | 1.58 (1.04-2.39) | 0.03 |
| Model 4 (n = 721) | Model 3 & BNP | 1.57 (1.01-2.44) | 0.04 |

*HR = hazard ratio;
$1^{st}$ quartile NRG-1β defined as NRG-1β < 3.4 ng/ml;
$4^{th}$ quartile NRG-1β > 8.6 ng/ml;
CI = confidence interval

Example 5

Interaction by Cardiomyopathy Etiology and Heart Failure Severity in the Penn Heart Failure Study Given the underlying biological differences between ischemic and nonischemic heart failure and the changes in compensatory mechanisms as heart failure progresses, we postulated that the role of NRG-1β might differ according to heart failure etiology and severity of disease. Interaction terms were introduced between NRG-1β and heart failure etiology (ischemic versus nonischemic) and NRG-1β and NYHA Class (I/II versus II/IV) in our Cox models.

The relationship between NRG-1β and risk of death or transplantation differed significantly according to cardiomyopathy etiology in both unadjusted and multivariable adjusted analyses (adjusted interaction p=0.008, Table 7). In patients with ischemic heart failure, there was an elevated risk of death or transplant with higher circulating NRG-1β, with an adjusted HR of 1.67(1.24-2.26, p=0.001) per Ln(NRG-1β). By contrast, in patients with nonischemic heart failure, there was no significant association (HR 0.98, 0.76-1.27, p=0.88). Similarly, the relationship between NRG-1β and risk of death or transplantation differed by heart failure severity (adjusted interaction p=0.01, Table 7). Patients with NYHA III/IV symptoms demonstrated a HR of 1.40 (1.11-1.76, p=0.005), whereas patients with NYHA I/II showed no significant association (HR 0.84, 0.61-1.16, p=0.28). Thus, the associations between NRG-1β and adverse outcomes were most evident in patients with ischemic heart failure and in patients with more advanced disease.

TABLE 7

Associations between NRG-1β and risk of death or cardiac transplantation according to heart failure etiology and severity.

| Model | Adjusted HR (95% CI) per 1-unit increment in Ln(NRG-1β)* | Interaction P-value |
|---|---|---|
| Entire cohort (n = 721) | 1.25 (1.02-1.53) | |
| Stratified by Etiology | | |
| Nonischemic (n = 482) | 0.98 (0.76-1.27) | 0.008 |
| Ischemic (n = 239) | 1.67 (1.24-2.26) | |

TABLE 7-continued

Associations between NRG-1β and risk of death or cardiac transplantation according to heart failure etiology and severity.

| Model | Adjusted HR (95% CI) per 1-unit increment in Ln(NRG-1β)* | Interaction P-value |
|---|---|---|
| Stratified by NYHA Class | | |
| Class I/II (n = 421) | 0.84 (0.61-1.12) | 0.01 |
| Class III/IV (n = 300) | 1.40 (1.11-1.76) | |

*Adjusted for covariates listed in Table 6, Model 4;
HR = hazard ratio;
CI = confidence interval Example 6

NRG-1β and Circulating BNP in the Penn Heart Failure Study

Higher BNP levels were associated with a significant risk of death or transplant, with a HR per Ln(BNP) of 1.64 (1.47-1.84, p<0.001). However, the Spearman correlation coefficient between BNP and NRG-1β was only 0.09 (p=0.02), suggesting a weak relationship between these two biomarkers. In addition, the association between NRG-1β and risk of death or transplantation was independent of BNP (Table 6, Model 4).

Because baseline levels of NRG-1β and BNP may measure different aspects of heart failure pathophysiology, the combined influence of NRG-1β and BNP was tested on risk of transplant-free survival, with the objective of exploring the potential additive effects of both markers. Based on results from our previous tests for interaction, these analyses were stratified according to heart failure etiology and severity.

Figure 6:
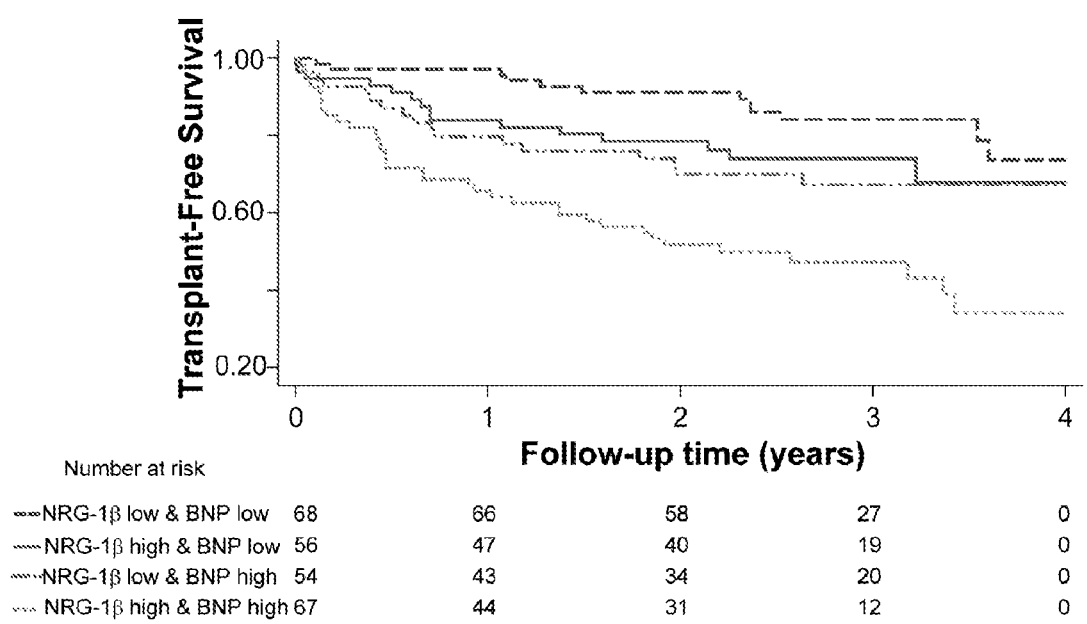
FIG. 6. Shows, the combined effects of NRG-1β and BNP on transplant-free survival in ischemic heart failure (n=245). $p<0.001$ by the log-rank test.

The ischemic and nonischemic groups were each divided into four sub-groups based on median cutpoints of NRG-1β and BNP. In ischemic heart failure, NRG-1β provided an additive effect to BNP in defining risk of adverse outcomes in both Kaplan-Meier (FIG. 6) and multivariable adjusted models (Table 8). The adjusted HR for patients with high NRG-1β and BNP levels was 3.88 (1.88-8.07, p<0.001) compared to patients with low levels of both biomarkers, while the risk was 1.53 (0.68-3.46, p=0.30) in those with low NRG-1β and high BNP. There was no clear additive effect of NRG-1β and BNP assessment in nonischemic heart failure.

TABLE 8

Combined effects of NRG-1β and BNP on risk of death or cardiac transplantation according to cardiomyopathy etiology

| | Nonischemic | | Ischemic | |
|---|---|---|---|---|
| Group* | N | Adjusted HR (95% CI)† | N | Adjusted HR (95% CI)† |
| Low NRG-1β & Low BNP | 124 | 1 (reference) | 67 | 1 (reference) |
| High NRG-1β & Low BNP | 117 | 1.08 (0.36-3.24) | 54 | 1.63 (0.73-3.65) |
| Low NRG-1β & High BNP | 116 | 5.37 (2.34-12.32) | 54 | 1.53 (0.68-3.46) |
| High NRG-1β & High BNP | 125 | 4.78 (2.06-11.10) | 64 | 3.88 (1.86-8.07) |

Figure 7:
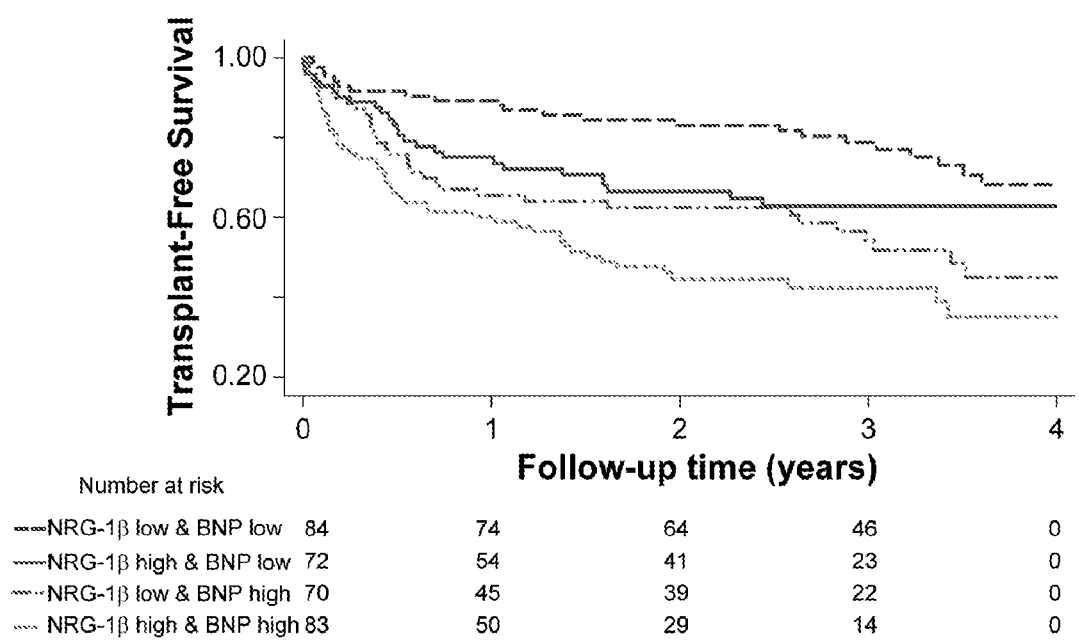
FIG. 7. Shows the combined Effects of NRG-1β and BNP on transplant-free survival in NYHA III/IV heart failure (n=309). $p<0.001$ by the log-rank test.

*Low/High NRG-1β defined as below/above median (5.2 ng/ml in nonischemics; 4.9 ng/ml in ischemics Low/High BNP defined as below/above median (82.7 pg/ml in nonischemics; BNP = 246.8 pg/ml in ischemics).
†Adjusted for covariates in Table 6, Model 3;
HR = hazard ratio;
CI = confidence interval Similarly, the NYHA III/IV and NYHA I/II groups were each divided into four sub-groups based upon their median outpoints of NRG-1β and BNP. In NYHA III/IV heart failure, NRG-1β provided an additive effect to BNP in defining risk of adverse outcomes in both Kaplan-Meier (FIG. 7) and multivariable adjusted models (Table 9). The adjusted HR for patients with high NRG-1β and BNP was 2.79 (1.62-4.79, p<0.001) compared to patients with low levels of each marker, while the risk was 1.79 (0.99-3.22, p=0.06) in those with low NRG-1β and high BNP. There was no clear additive value to NRG-1β to BNP assessment in NYHA I/II heart failure. Thus, NRG-1β and BNP in combination were superior to either biomarker alone in describing the risk of adverse outcomes in patients with ischemic heart failure or NYHA III/IV symptoms.

TABLE 9

Combined effects of NRG-1β and BNP on risk of death or cardiac transplantation according to heart failure severity.

| | NYHA I/II | | NYHA III/IV | |
|---|---|---|---|---|
| Group* | N | Adjusted HR (95% CI)† | N | Adjusted HR (95% CI) |
| Low NRG-1β & Low BNP | 106 | 1 (reference) | 82 | 1 (reference) |
| High NRG-1β & Low BNP | 104 | 0.23 (0.03-2.02) | 69 | 1.69 (0.92-3.12) |
| Low NRG-1β & High BNP | 103 | 1.89 (0.63-5.67) | 70 | 1.79 (0.99-3.22) |
| High NRG-1β & High BNP | 108 | 1.79 (0.56-5.74) | 79 | 2.79 (1.62-4.79) |

†Adjusted for covariates in Table 6, Model 3;
HR = hazard ratio;
CI = confidence interval Altogether, the data in 899 PHFS subjects indicate that circulating NRG-1β is a marker of heart failure severity with independent associations with NYHA class and adverse clinical outcomes. These data demonstrate the performance of the NRG-1β assay across a diverse cohort of subjects with heart failure, with achievement of a desired coefficient of variation of 5.6%. These are the first data demonstrating that NRG-1β is clinically relevant to human heart failure, and identify circulating NRG-1β as a marker of heart failure severity, with novel associations between higher NRG-1β levels and advanced NYHA Class, adverse outcomes, and worse cardiac function. Subgroups were identified where the relationship between NRG-1β and adverse outcomes may be most informative, i.e. ischemic heart failure and advanced NYHA Class.

Example 7

Chronic Renal Insufficiency Cohort (CRIC)

The CRIC study is a multi-center prospective cohort study established to study the progression of cardiovascular and renal disease among patients with chronic renal insufficiency. Subjects are recruited based upon age-related entry criteria for glomerular filtration rate. There are approximately 3612 subjects at baseline, and they are followed for up to 5 years. Recruitment was initiated in 2003 and completed in March 2007. Exclusion criteria include life expectancy less than 3 years, NYHA class III or IV heart failure, known cirrhosis, known HIV, prior end stage renal disease, prior organ or bone marrow transplant, immunosuppressive therapy within the prior 6 months, chemotherapy within the past 2 years, polycystic kidney disease, pregnancy and institutionalized patients. Subjects undergo extensive baseline clinical evaluations and return annually for in-person follow-up visits. Telephone interviews take place every 6 months to query about study outcomes and updates on general health. All subjects undergo transthoracic echocardiograms at Years 1 and 4 post-enrollment. These echocardiograms then undergo rigorous quantitative assessment at the Penn Center for Quantitative Echocardiography.

The CRIC study organization consists of the Scientific Data Coordinating Center (SDCC) and seven clinical centers. In this cohort, approximately 55% of the subjects are males, and the mean age is 58 years. There are 45% Caucasians and 47% African-Americans. There is a predominance of hypertension (87%) and diabetes (48%). Preliminary year 1 echo data (n=684) reveal 28.6% of the cohort have normal remodeling geometry, 19.8% concentric remodeling, 29.3% concentric hypertrophy and 22.2% have eccentric hypertrophy.

In terms of clinical outcomes, as of January 2009, there have been 322 deaths over 7,450 person years. A total of 306 hospitalizations for heart failure have been reported to date. In addition, there have been 181 hospitalizations for coronary disease, 213 for arrhythmias, and 780 hospitalizations for the composite endpoint of coronary disease, heart failure, arrhythmia, stroke, or peripheral vascular disease.

Example 8

NRG-1β is Hypothesized to be Associated with Response and Change in Cardiac Growth and Remodeling in CRIC In the $2^{nd}$ study (see FIG. 2) NRG-1β is associated with response and change in cardiac growth and remodeling within a cohort of individuals from CRIC. A random sample of subjects are chosen to conduct the analyses. The analysis is stratified by ventricular geometry, namely normal, concentric remodeling, concentric hypertrophy, and eccentric hypertrophy. Given that Year 1 remodeling geometries are distributed fairly evenly (~20-29%) across the CRIC study, a random sample provides equal representation of subjects across each of the geometries. For this study, stratified analyses will be important given that the biology of remodeling may differ according to ventricular geometry. All four remodeling geometries in the $2^{nd}$ study are included because of the presence of longitudinal data, including serial echocardiograms and repeated measures of NRG-1β that are available in CRIC but not PHFS.

Figure 8:
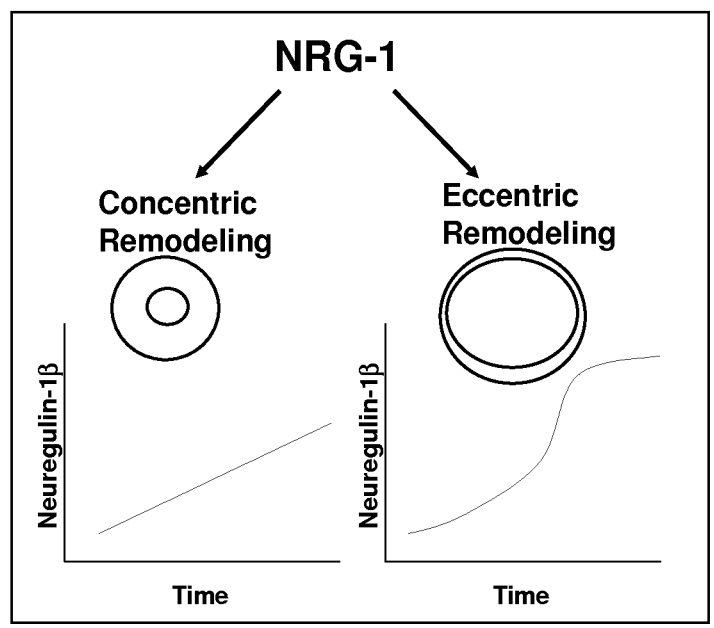
FIG. 8 shows concrete and eccentric remodeling over time.

Following the studies, it is hypothesized that circulating NRG-1β levels are associated with progressive concentric cardiac remodeling and hypertrophy in a linear fashion, whereas the trajectory of circulating NRG-1β over time in eccentric hypertrophy is more complex and nonlinear (FIG. 8).

Example 9

Figure 2:
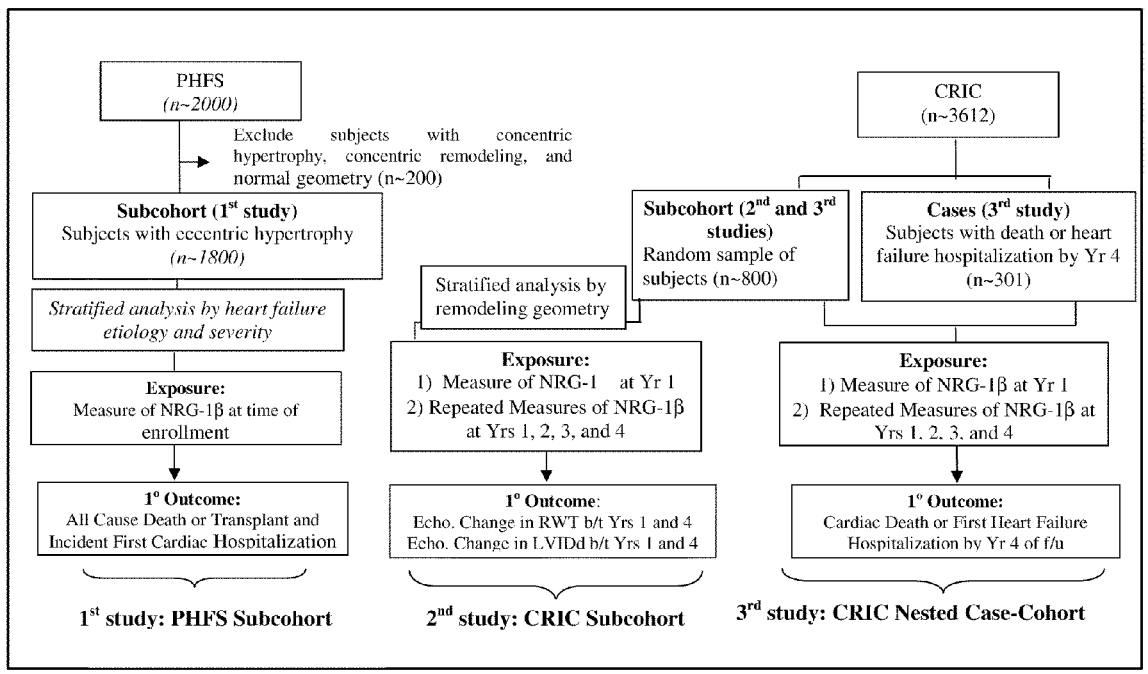
FIG. 2. Shows a comprehensive study of NRG-1β in the Penn Heart Failure Study (PHLS) and the Chronic Renal Insufficiency Cohort (CRIC) subjects which together represent the entire spectrum of remodeling.

Sustained Elevations in Circulating NRG-1β Levels are Hypothesized to be Independently Associated with a Subsequent Increase Risk of Hospitalization for Heart Failure and Cardiovascular Health In the $3^{rd}$ study which involves CRIC, the entire spectrum of cardiac remodeling are assessed and the associations between NRG-1β and clinical outcomes via a case-cohort study are determined. A case-cohort design preserves our ability to study multiple outcomes and use our resources most efficiently by studying a random sample of the entire CRIC population (the cohort) and all cases of disease (first heart failure hospitalization and cardiovascular death). The subcohort used for the $3^{rd}$ study is the same cohort as the $2^{nd}$ study, and represents a random sample of all CRIC subjects (FIG. 2). Use of the same subjects in the $2^{nd}$ and $3^{rd}$ studies maximizes efficiency. The cases are those subjects who have developed the outcomes of interest, cardiac death or heart failure hospitalization, by Year 4 of follow-up. As part of the secondary analyses, the possibility of effect modification by remodeling geometry is assessed, where the study comprises approximately 200 subjects per stratum to perform analyses.

An added major advantage of the case-cohort study design over case-control studies is the ability to study multiple endpoints by using the same subcohort for several disease outcomes. CRIC has data on multiple other potentially relevant outcomes (such as myocardial infarction and major arrhythmic events), and a case-cohort study allows assessment of multiple endpoints. The case-cohort approach has commonly been used in large cohort studies such as Atherosclerosis Risk in Communities study (ARIC) and provides an unbiased estimate of the relative risk.

A case-cohort design is used to accomplish in the $3^{rd}$ study to assess clinical outcomes in CRIC, and the same cohort is used to study echocardiography outcomes for the $2^{nd}$ study. Thus, the randomly sampled cohort is used in both $2^{nd}$ and $3^{rd}$ studies. A random sample of the cohort should provide a fairly uniform distribution of subjects with normal, concentric remodeling, concentric hypertrophy, and eccentric hypertrophy to address the $2^{nd}$ study and perform exploratory analyses in the $3^{rd}$ study.

Example 10

Chemotherapy-Induced Heart Failure

It has been observed that patients with chemotherapy-induced heart failure (n=17) from the Penn Heart Failure Study have significant alterations in NRG-1β as compared to all other etiologies. In addition, a prospective cohort of breast cancer patients exposed to chemotherapy (doxorubicin and trastuzumab) are followed every 3 months. In this prospective cohort, increases in circulating NRG-1β plasma levels over time are associated with incident cardiac dysfunction.

To determine the contribution of variation in NRG/ErbB signaling on risk of cancer therapy-induced cardiac dysfunction, the relationship between SNP/haplotype variation in NRG/ErbB genetics and incident cardiac dysfunction is quantified. The clinical, predictive utility of potential risk variants in this important population is determined. As a result, it is observed that patients who develop incident cardiac dysfunction have elevated levels of circulating NRG-1β with exposure to chemotherapy, demonstrating that NRG-1β is indicative of cardiac stress and is a marker of dysfunction. The predictive value of an integrated biomarker and a genetic approach are explored. This knowledge facilitates care of patients by personalizing the use of cancer therapy to minimize cardiotoxicity (e.g. alternative regimens for those patients at high risk for cardiotoxicity); identifying patients who benefit from early cardioprotective strategies; and overall improving the cardiovascular health of this population.

Example 11

The Relevance of NRG-1β in Cancer Therapy Cardiotoxicity

Development of novel mechanistic markers (circulating proteins, genetic variations, sensitive imaging parameters)

may help improve our understanding of the disease and be useful in risk stratification, as a multi-marker strategy. NRG-1 is paracrine epidermal growth factor whose effects are mediated by the ErbB family of tyrosine kinase receptors. This pathway is necessary for cardiac development, critical for stress-responsiveness, cardiac growth, and maintenance of function. Our data in 899 subjects from the Penn Heart Failure Study show that in chronic systolic heart failure, higher circulating levels of NRG-1β are independently associated with heart failure severity and an increased risk of all-cause death or cardiac transplantation.

Objective/Aim:

The objective of the study was to determine the clinical relevance of circulating neuregulin-1β (NRG-1β) as it relates to chemotherapy cardiotoxicity. The aim was to establish the relationship between circulating NRG-1β and incident adverse cardiovascular events in subjects exposed to doxorubicin and trastuzumab.

Methods:

Breast cancer patients receiving doxorubicin followed by trastuzumab were prospectively recruited. Echocardiograms and measures of plasma NRG-1β were performed at 3 timepoints: prior to doxorubicin, prior to trastuzumab, and after 3 months of trastuzumab.

Figure 9:
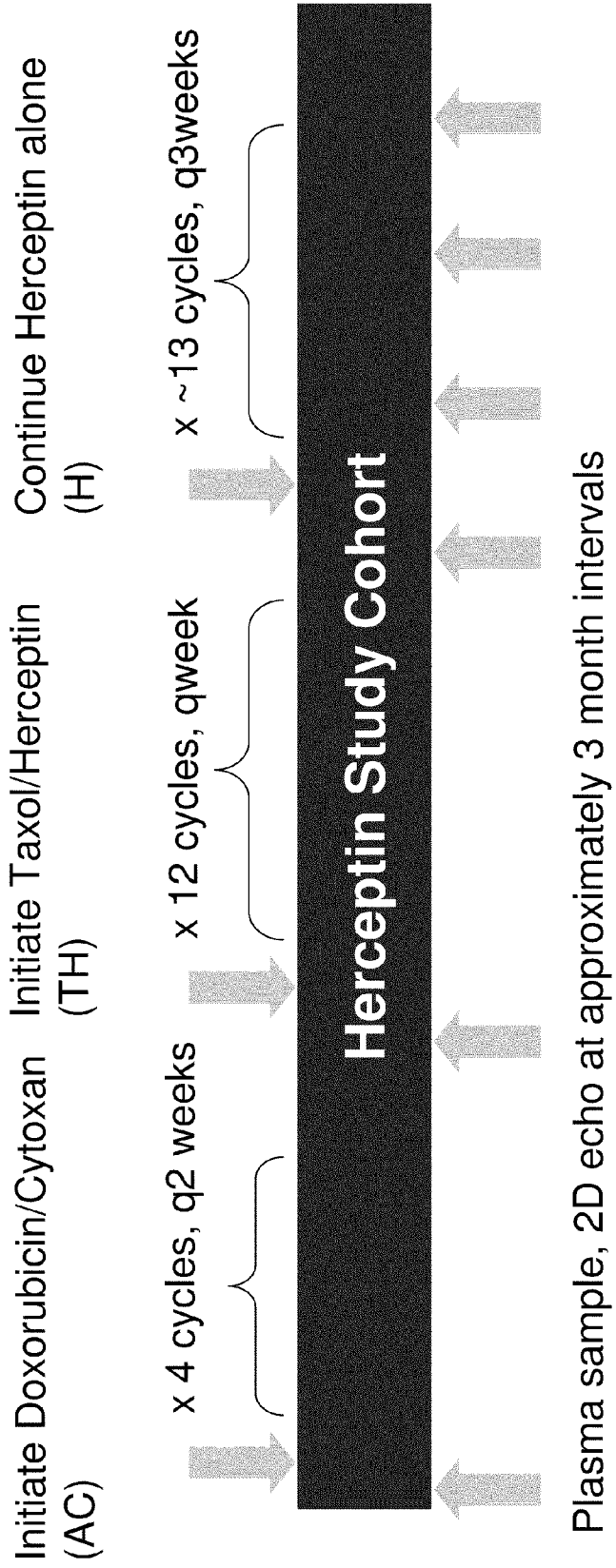
FIG. 9 shows herceptin cardiac research study.
Figure 10:
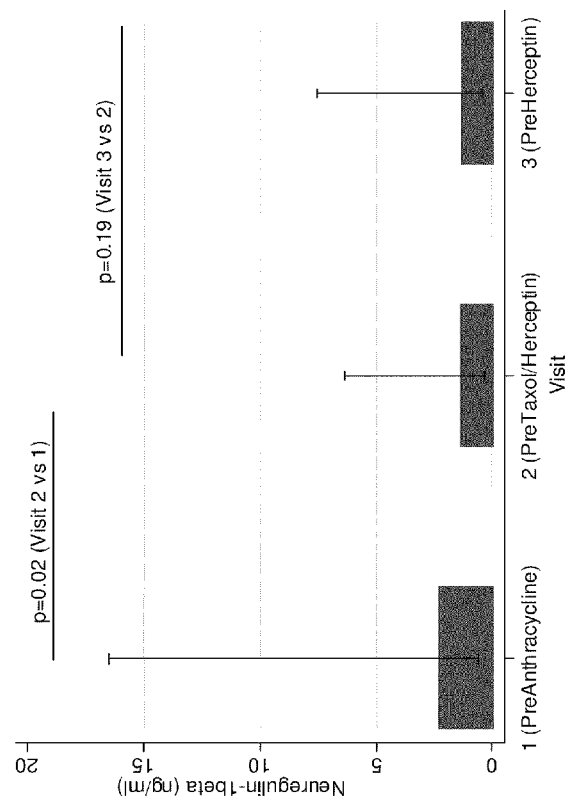
FIG. 10 shows changes in NRG-1β with doxorubicin and trastuzumab exposure.

Multi-center observational cohort study of Her-2+ breast cancer outpatients receiving doxorubicin and trastuzumab is shown in FIG. 9. As shown in FIG. 9, measures of plasma NRG-1β were obtained at 3 timepoints: Pre Doxorubicin, Pre Taxol/Herceptin, and after 3 months of Taxol/Herceptin. Data were obtained at enrollment and every 3 months during anticancer therapy.

NRG-1β plasma level was measured serially every 3 months during chemotherapy treatment. NRG-1β was measured via indirect sandwich ELISA that detects a biologically active peptide sequence highly expressed in cardiac system (CV 5.6-13%).

Tests were performed to determine incident cardiotoxicity. Incident cardiotoxicity can be defined as symptomatic heart failure or asymptomatic decline in left ventricular ejection fraction (EF) including a ≥10% to less than 50% or >15% from baseline. Serial measures of EF were obtained every 3 months, measured using Simpson's biplane method of discs.

Results:

Of the 12 patients, 1 experienced cardiac dysfunction, as defined by a decline in EF by >10% to <55%. In this patient, a significant 6-fold increase in NRG-1β over time was observed. In those who maintained normal cardiac function, absolute NRG-1β levels were lower, with minor changes in serial measures. Patient characteristics are shown below.

TABLE 1

Patient Characteristics (n = 39)

| Characteristic | Mean ± s.d. or Number (%) |
| --- | --- |
| Age (yrs) | 49 ± 10 |
| Hypertension, n (%) | 11 (28%) |
| Hyperlipidemia, n (%) | 7 (18%) |
| Cardiac Medication, n (%) | 10 (26%) |
| Tobacco Use, n (%) | 6 (13%) |
| Chemotherapy Regimen, n (%) | |
| AC-TH-H | 32 (82%) |
| TH-AC-H | 4 (10%) |
| Prior AC therapy | 3 (8%) |
| Radiation, n (%) | 4 (10%) |

Figure 11:
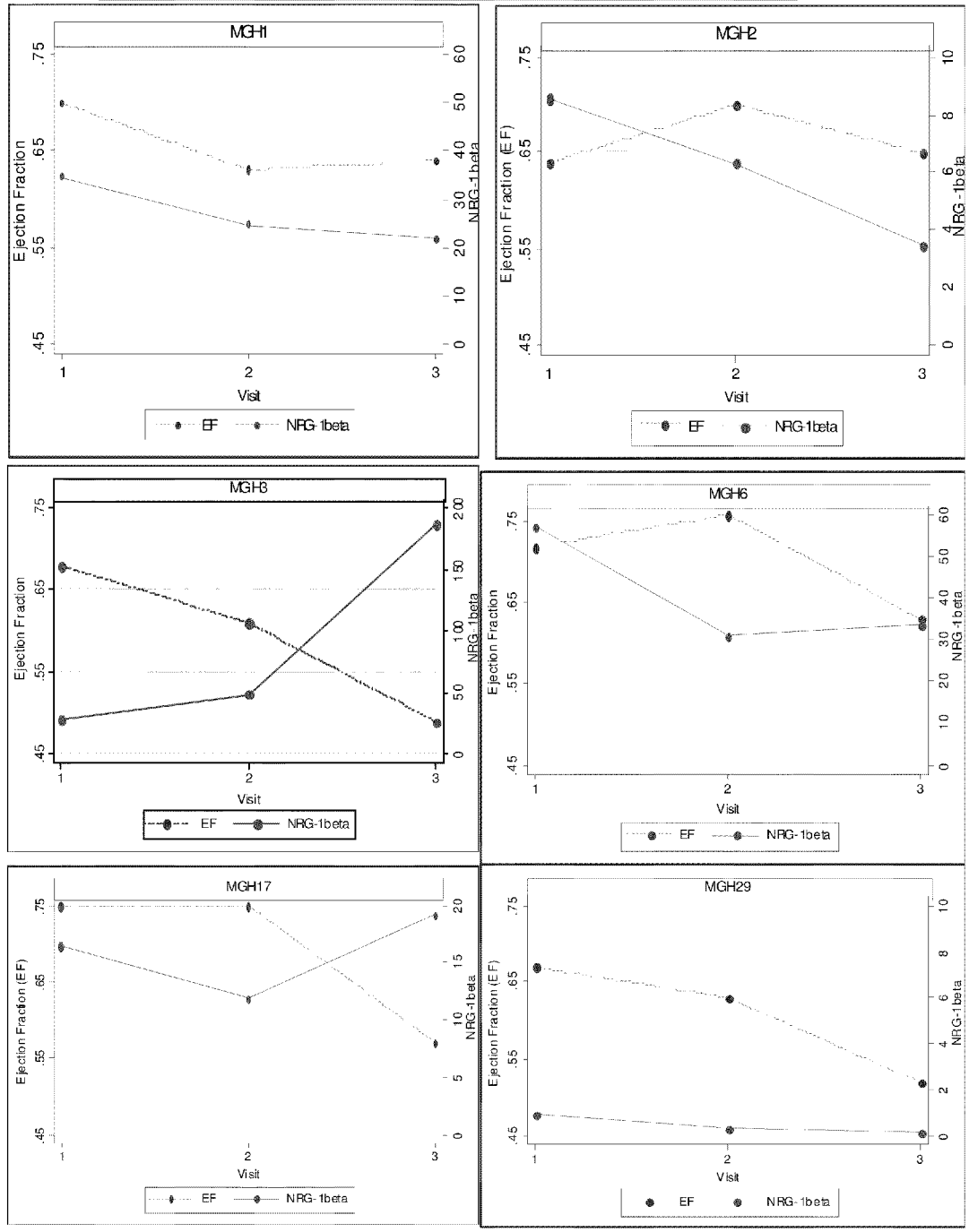
FIG. 11 shows changes in NRG-1β and ejection fraction with (a) doxorubicin and herceptin in MGH patients; (b) doxorubicin and herceptin in montreal patients; and (c) herceptin therapy prior to doxorubicin.
Figure 11:
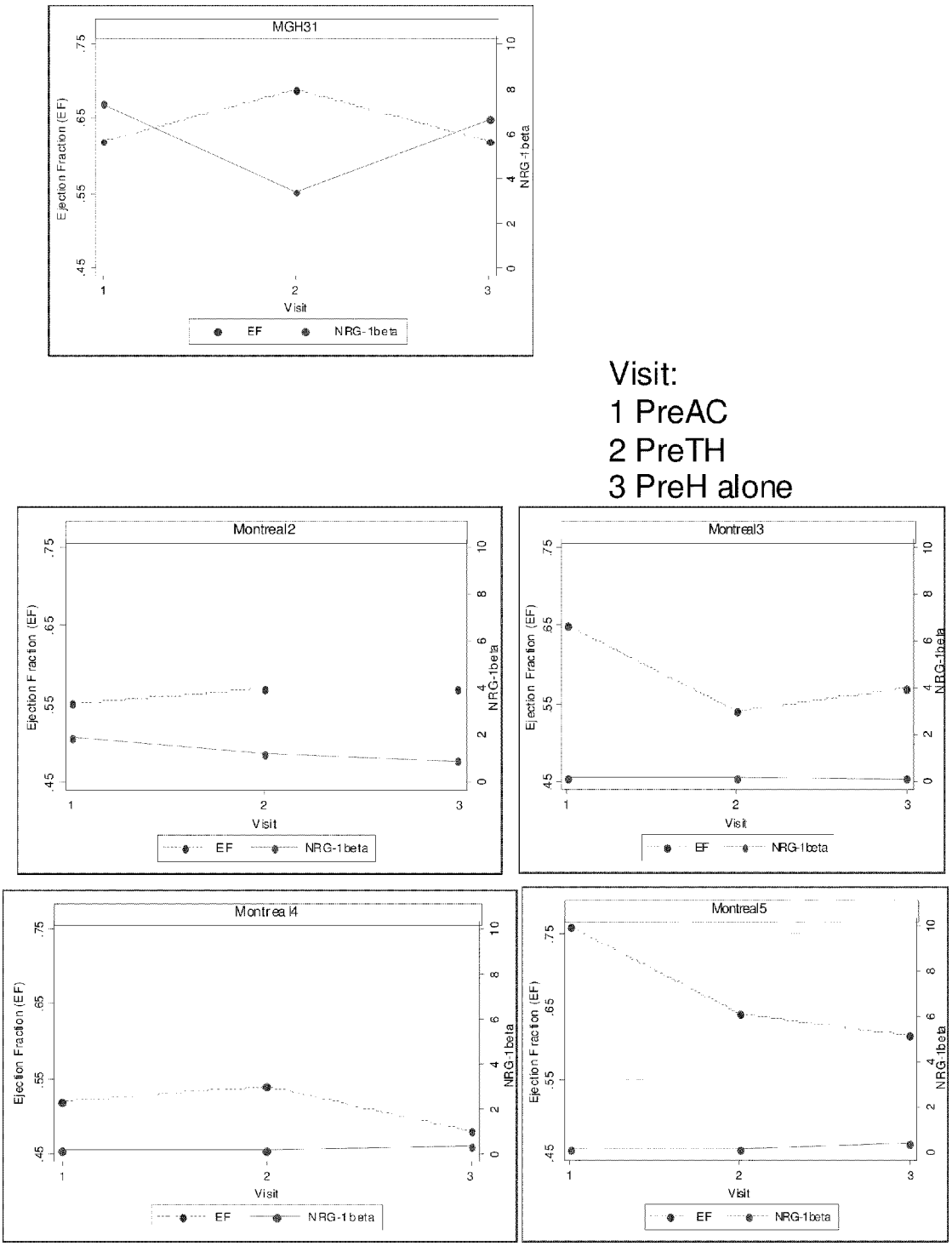
Figure 11:
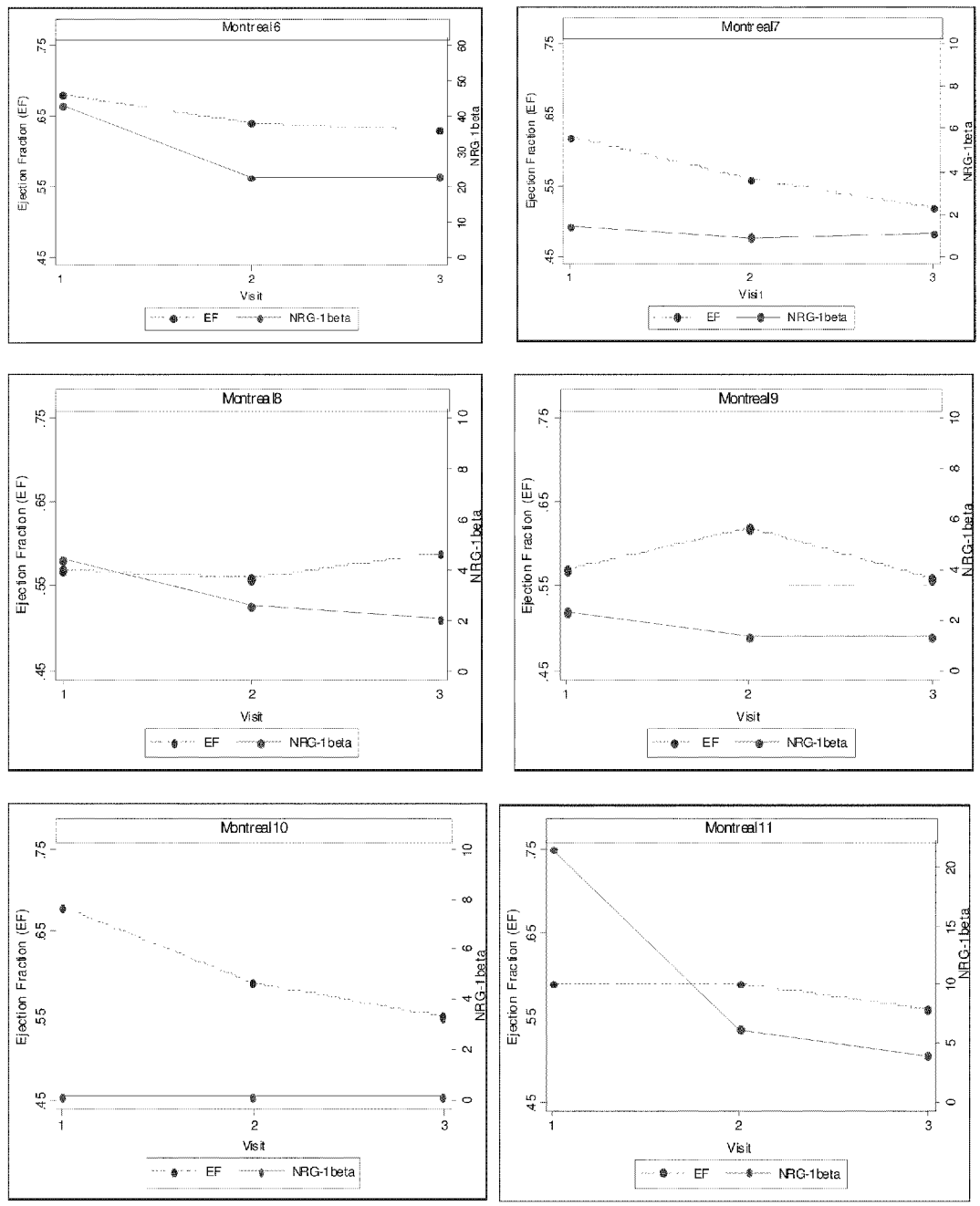
Figure 11:
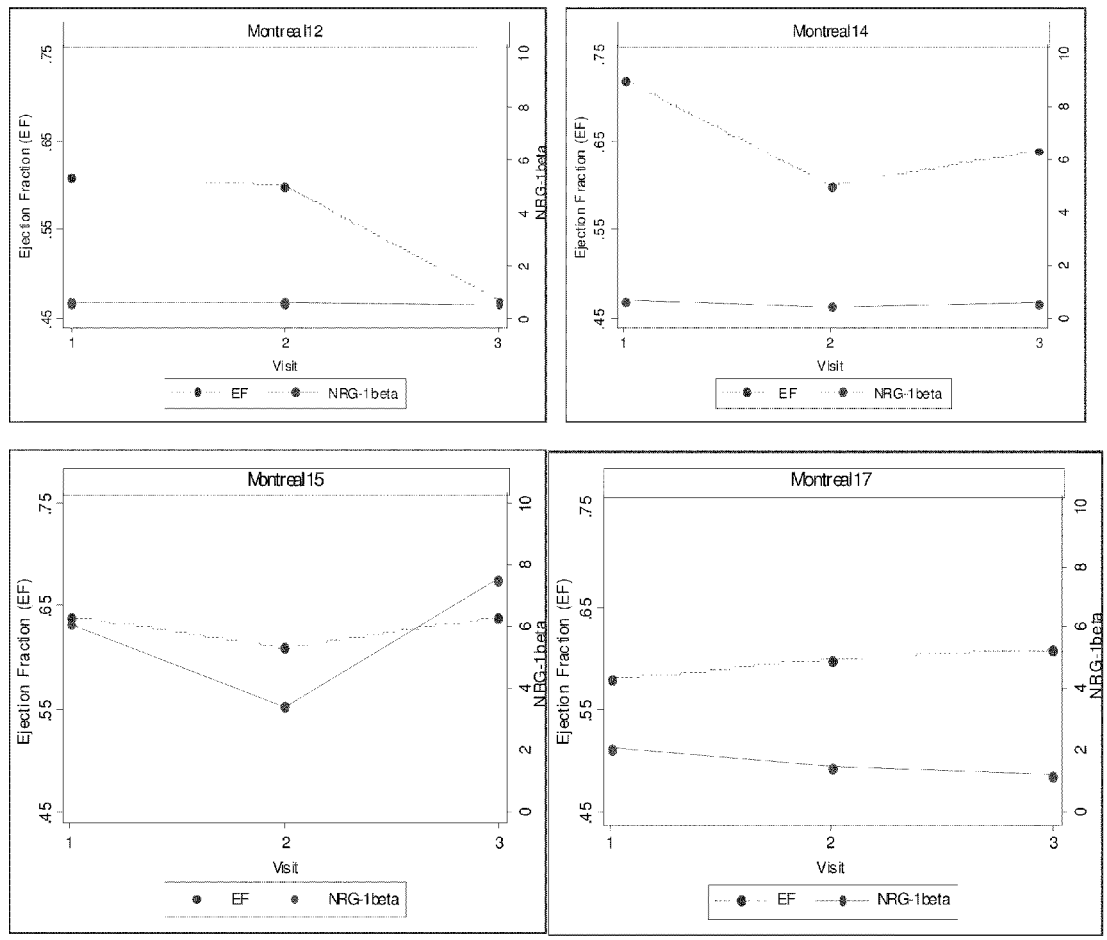

Our results indicated that, with Doxorubicin exposure, there was a significant decrease in NRG-1β over time. Three months of Herceptin exposure was not associated with a statistically significant change in NRG-1β. Example of changes in NRG-1β and EF with Doxorubicin and Trastuzumab exposure according to individual patients displayed in FIG. 11.

Our results show that doxorubicin is associated with a significant decline in NRG-1β levels, indicative of endothelial dysfunction and alteration of NRG-1β production. With increased cardiac stress, there may be an increase in circulating NRG-1β as a compensatory response.

Our results further show that circulating NRG-1β may be altered in patients at risk for trastuzumab-induced cardiotoxicity and provides mechanistic insight into the cardiotoxic effects of trastuzumab.

Having described the embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for providing a prognosis of heart failure severity in a subject having suffered from heart failure, said method comprising:
    obtaining a biological sample from said subject;
    contacting said sample with an antibody that specifically binds to Neuregulin-1β(NRG-1β) to form an antibody-NRG-1β complex;
    measuring the amount of the antibody-NRG-1β complex to determine the level of expression of NRG-1β in the subject; and
    comparing said level of expression of NRG-1β in the subject to that of a pre-determined standard to determine the level of NRG-1β over-expression or under-expression in said subject relative to the standard;
    determining the heart failure severity in the subject, wherein the level of over-expression of NRG-1β in the subject indicates the heart failure severity in the subject.

2. The method of claim 1, further comprising the steps of measuring the level of expression of BNP in the sample compared to a standard for BNP expression, and determining the heart failure severity in the subject based on the expression levels of both NRG-1β and BNP, thereby improving the indication of heart failure severity over either NRG-1β or BNP alone.

3. The method of claim 1, wherein said heart failure is ischemic heart failure or nonischemic heartfailure, hypertensive heart disease, inflammatory heart disease, valvular heart disease, coronary heart disease, cardiomyopathy, cardiovascular disease, or chemotherapy-related disease.

4. The method of claim 1, wherein the level of expression of NRG-1β is independently associated with transplant-free survival.

5. The method of claim 1, wherein said subject is being monitored for the severity of heart failure.

6. The method of claim 1, wherein said subject is undergoing chemotherapeutic therapy.

7. The method of claim 1, wherein said biological sample is blood, sera, plasma, tissue biopsy, organ biopsy or a combination thereof.

8. The method of claim 1, whereby the standard is taken from a subject or pool of subjects correctly diagnosed as being healthy.

9. The method of claim 1, wherein sustained over-expression in circulating NRG-1β levels are associated with a subsequent increased risk of hospitalization for heart failure and cardiovascular death.

10. The method of claim 1, wherein circulating NRG-1β levels are associated with progressive concentric cardiac remodeling and hypertrophy in a linear fashion in said subject.

11. The method of claim 1, wherein said antibody that specifically binds to Neuregulin-1β is not cross-reactive with NRG-1α or epidermal growth factor.

12. The method of claim 1, wherein the contacting and measuring steps comprise performing an immunoassay selected from the group consisting of enzyme immune assay (EIA), a radioimmune assay (RIA), a Western blot assay, and a slot blot assay.

13. The method of claim 12, wherein the immunoassay is an enzyme-linked immunosorbent assay (ELISA).

14. The method of claim 13, wherein the ELISA is an indirect sandwich ELISA.

* * * * *

UNITED STATES PATENT AND TRADEMARK OFFICE
CERTIFICATE OF CORRECTION

| | | Page 1 of 1 |
|---|---|---|
| PATENT NO. | : 8,962,257 B2 | |
| APPLICATION NO. | : 13/043350 | |
| DATED | : February 24, 2015 | |
| INVENTOR(S) | : Bonnie Ky | |

It is certified that error appears in the above-identified patent and that said Letters Patent is hereby corrected as shown below:

Specification

In column 1, lines 11-17 should be replaced with the following paragraph:

GOVERNMENT INTEREST STATEMENT

This invention was made with government support under grant numbers HL088577, HL068144, RR024132 and HL095661 awarded by the National Institute of Health. The government has certain rights in the invention.

Signed and Sealed this
Tenth Day of November, 2015

Michelle K. Lee
*Director of the United States Patent and Trademark Office*